US011285199B2

(12) United States Patent
Moon et al.

(10) Patent No.: US 11,285,199 B2
(45) Date of Patent: Mar. 29, 2022

(54) **VACCINE COMPOSITION COMPRISING RECOMBINANT PROTEIN OF *STAPHYLOCOCCUS AUREUS* ATTENUATED ENTEROTOXIN AND CYTOTOXIN**

(71) Applicants: REPUBLIC OF KOREA (ANIMAL AND PLANT QUARANTINE AGENCY), Gyeongsangbuk-do (KR); Mississippi State University, Starkville, MS (US)

(72) Inventors: Dong Chan Moon, Gyeongsangbuk-do (KR); Suk Kyung Lim, Gyeongsangbuk-do (KR); Keum Chan Jang, Gyeonggi-do (KR); Suk Chan Jung, Gyeongsangbuk-do (KR); Hee Soo Lee, Gyeonggi-do (KR); Bang Hun Hyun, Gyeongsangbuk-do (KR); Hyang Mi Nam, Gyeongsangbuk-do (KR); Heui Jin Kim, Gyeongsangbuk-do (KR); Keun Seok Seo, Starkville, MS (US)

(73) Assignees: Republic of Korea (Animal and Plant Quarantine Agency); Mississippi State University, Starkville, MS (US)

( * ) Notice: Subject to any disclaimer, the term of this patent is extended or adjusted under 35 U.S.C. 154(b) by 0 days.

(21) Appl. No.: 16/972,887

(22) PCT Filed: Dec. 13, 2018

(86) PCT No.: PCT/KR2018/015865
§ 371 (c)(1),
(2) Date: Dec. 7, 2020

(87) PCT Pub. No.: WO2019/235705
PCT Pub. Date: Dec. 12, 2019

(65) Prior Publication Data
US 2021/0170010 A1 Jun. 10, 2021

(30) Foreign Application Priority Data
Jun. 8, 2018 (KR) .................. 10-2018-0066226

(51) Int. Cl.
*A61K 39/085* (2006.01)
*C07K 14/31* (2006.01)
*A61K 39/00* (2006.01)

(52) U.S. Cl.
CPC ............ *A61K 39/085* (2013.01); *C07K 14/31* (2013.01); *A61K 2039/552* (2013.01); *A61K 2039/55505* (2013.01)

(58) Field of Classification Search
None
See application file for complete search history.

(56) References Cited

U.S. PATENT DOCUMENTS

| 5,032,522 A | 7/1991 | Watson |
| 8,431,687 B2 * | 4/2013 | Torres ................... A61P 29/00 530/387.9 |
| 9,914,767 B2 * | 3/2018 | Nagy ................ C07K 16/1271 |
| 9,995,728 B2 * | 6/2018 | Fordham .......... G01N 33/48721 |
| 10,301,378 B2 * | 5/2019 | Torres ................... A61P 25/00 |
| 2014/0199339 A1 | 7/2014 | Schlievert et al. |

FOREIGN PATENT DOCUMENTS

KR 10-2018-0041972 A 4/2018

OTHER PUBLICATIONS

International Search Report and Written Opinion for corresponding International application No. PCT/KR2018/015865; dated May 27, 2019 (9 pages).
Dumont, Ashley L., et al. "Identification of a Crucial Residue Required for *Staphylococcus aureus* LukAB Cytotoxicity and Receptor Recognition." Infection and Immunity 82.3 (2014): 1268-1276.
Fernández, Marisa M., et al. "Crystal Structure of Staphylococcal Enterotoxin G (Seg) in Complex with a Mouse T-cell Receptor β Chain" Journal of Biological Chemistry 286.2 (2011): 1189-1195.
Lee Juyeun, et al. "Induction of Immunosuppressive CD8+ CD25+ FOXP3+ Regulatory T cells by Suboptimal Stimulation with Staphylococcal Snterotoxin C1" The Journal of Immunology 200.2 (2018): 669-680.

(Continued)

*Primary Examiner* — Padmavathi Baskar
(74) *Attorney, Agent, or Firm* — Mendelsohn Dunleavy, P.C.

(57) ABSTRACT

The present invention relates to a vaccine composition comprising a *Staphylococcus aureus* attenuated enterotoxin protein and cytotoxin protein, and more particularly to a *Staphylococcus aureus* enterotoxin protein, a *Staphylococcus aureus* cytotoxin protein, a vaccine composition for prevention of bovine mastitis, comprising the *Staphylococcus aureus* enterotoxin protein and *Staphylococcus aureus* cytotoxin protein and a method for preventing bovine mastitis comprising administering the vaccine composition to a bovine. The *Staphylococcus aureus* enterotoxin protein, the *Staphylococcus aureus* cytotoxin protein according to the present invention, and the vaccine composition comprising the proteins as an antigen can be used so that even vaccines comprising several antigens rather than all kinds of antigens show the excellent effects of prevention and treatment of bovine mastitis against all kinds of *Staphylococcus aureus* enterotoxin and cytotoxin having high incidence in Korea, thereby being more economically used for industrial purposes. Further, the vaccine composition for prevention of bovine mastitis, comprising the *Staphylococcus aureus* enterotoxin protein and *Staphylococcus aureus* cytotoxin protein according to the present invention has an excellent safety and bovine mastitis prevention and treatment effect even in the high CFU *Staphylococcus aureus* challenge test so that the composition can be variously utilized in *Staphylococcus aureus* vaccine and prevention related fields in future.

18 Claims, 9 Drawing Sheets

Specification includes a Sequence Listing.

(56) References Cited

OTHER PUBLICATIONS

Tuffs, Stephen W., et al. "The *Staphylococcus aureus* superantigen SEIX is a bifunctional toxin that inhibits neutrophil function." PLoS Tathogens 13.9 (2017): pp. e1006461 (28 pages).
GenBank: EVY84912.1 "leukotoxin LukE [*Staphylococcus aureus* T49833]", Feb. 25, 2014 (2 pages).
GenBank: SAZ82873.1 "Leukotoxin S subunit [*Staphylococcus aureus*]", May 18, 2016 (1 pages).
GenBank: BAB47174.1 "LukNS [*Staphylococcus aureus*]", May 8, 2001 (1 pages).
GenBank: AUM58020.1 "Panton-Valentine leukocidin chain S precursor [*Staphylococcus* phage phiSa2wa_st72]", Jan. 10, 2018 (2 pages).

* cited by examiner

[Fig. 1]
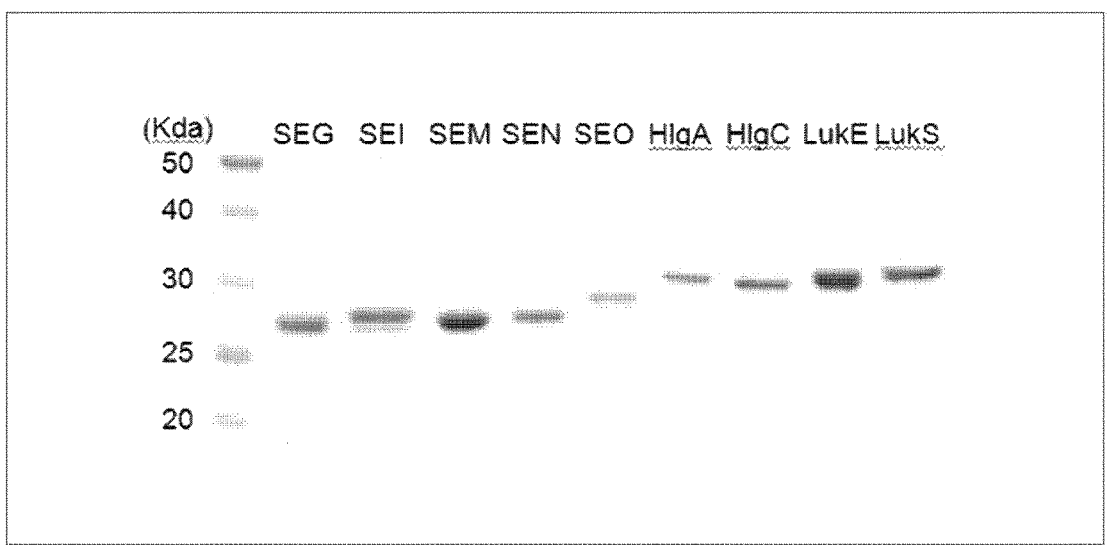
[Fig. 2]
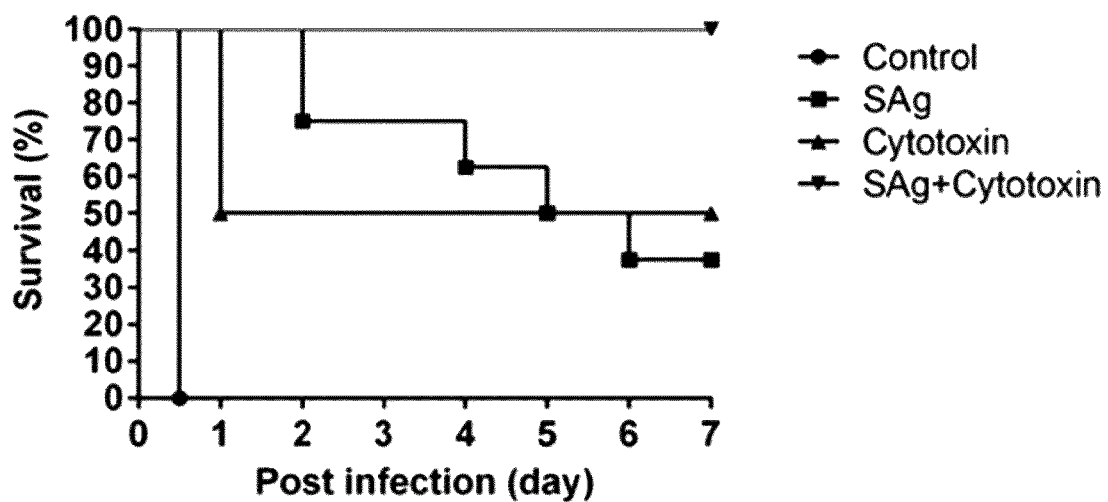
[Fig. 3]
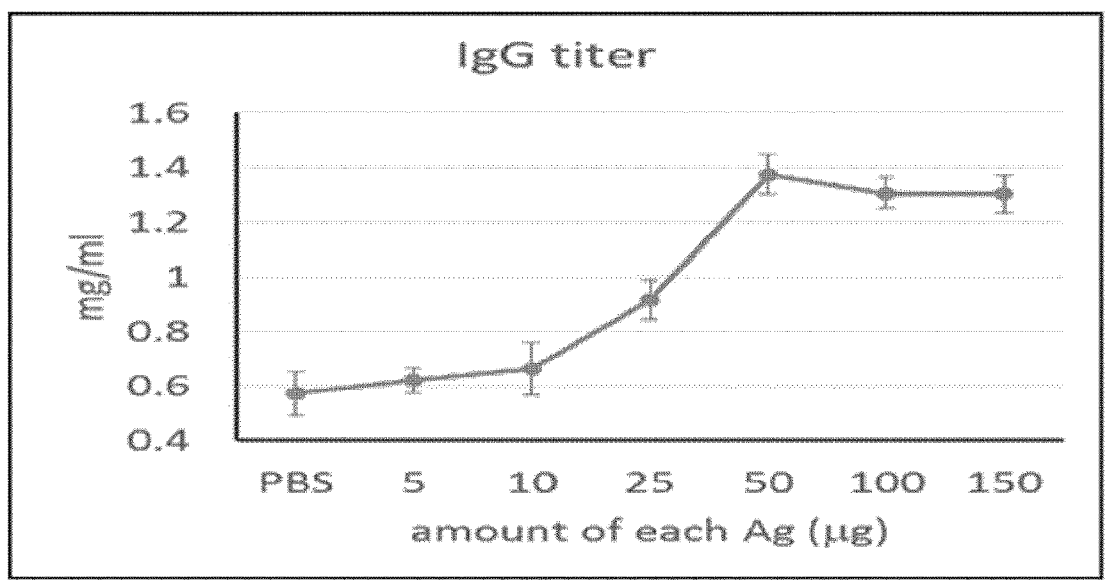

[Fig. 4]
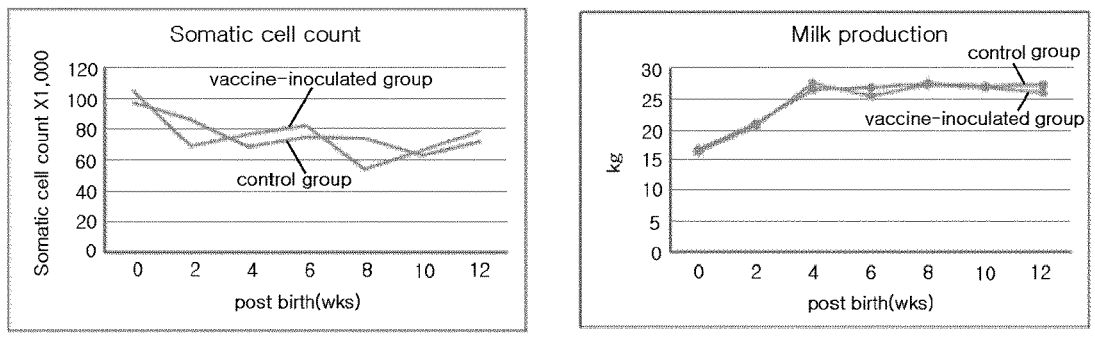
[Fig. 5]
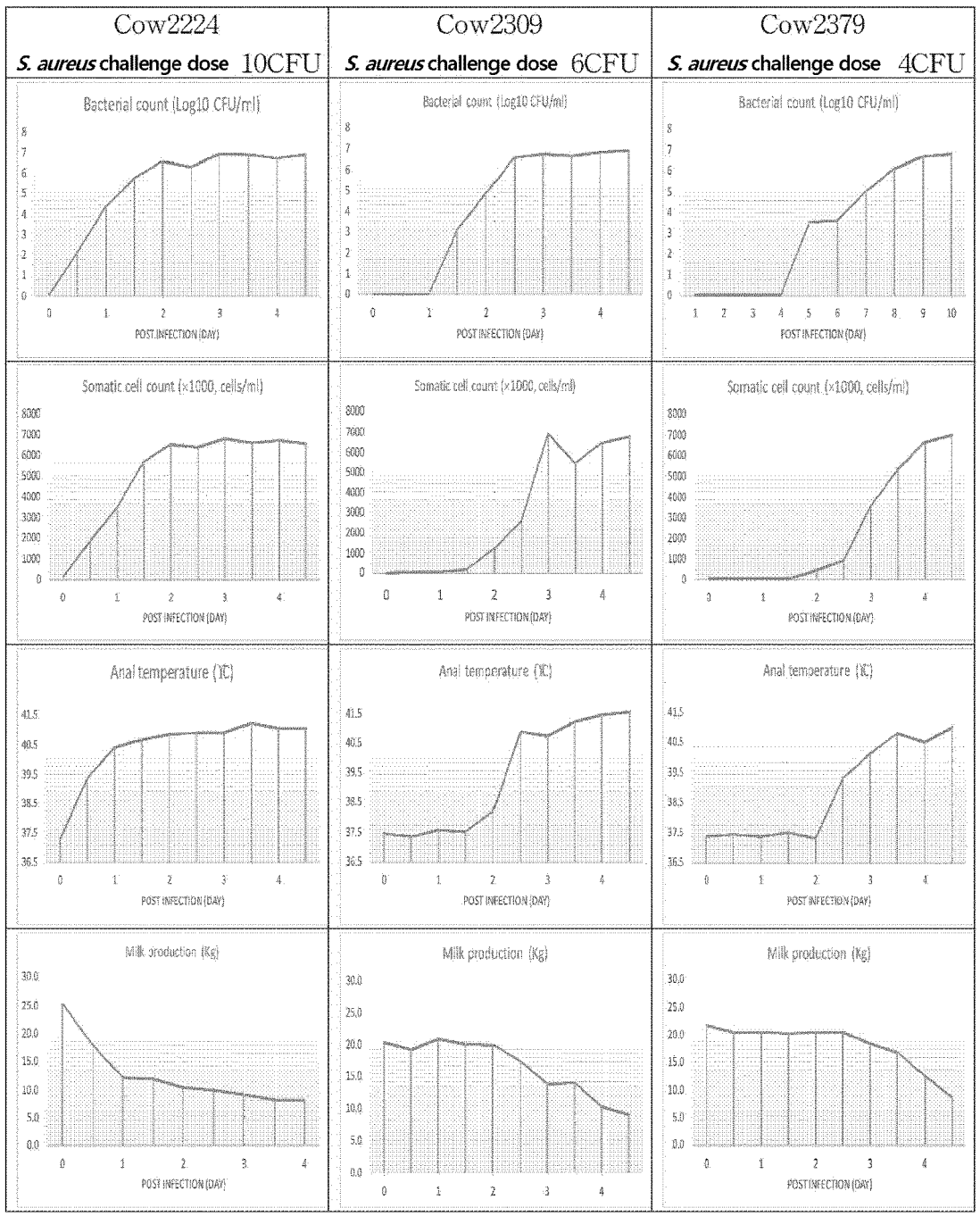

[Fig. 6a]
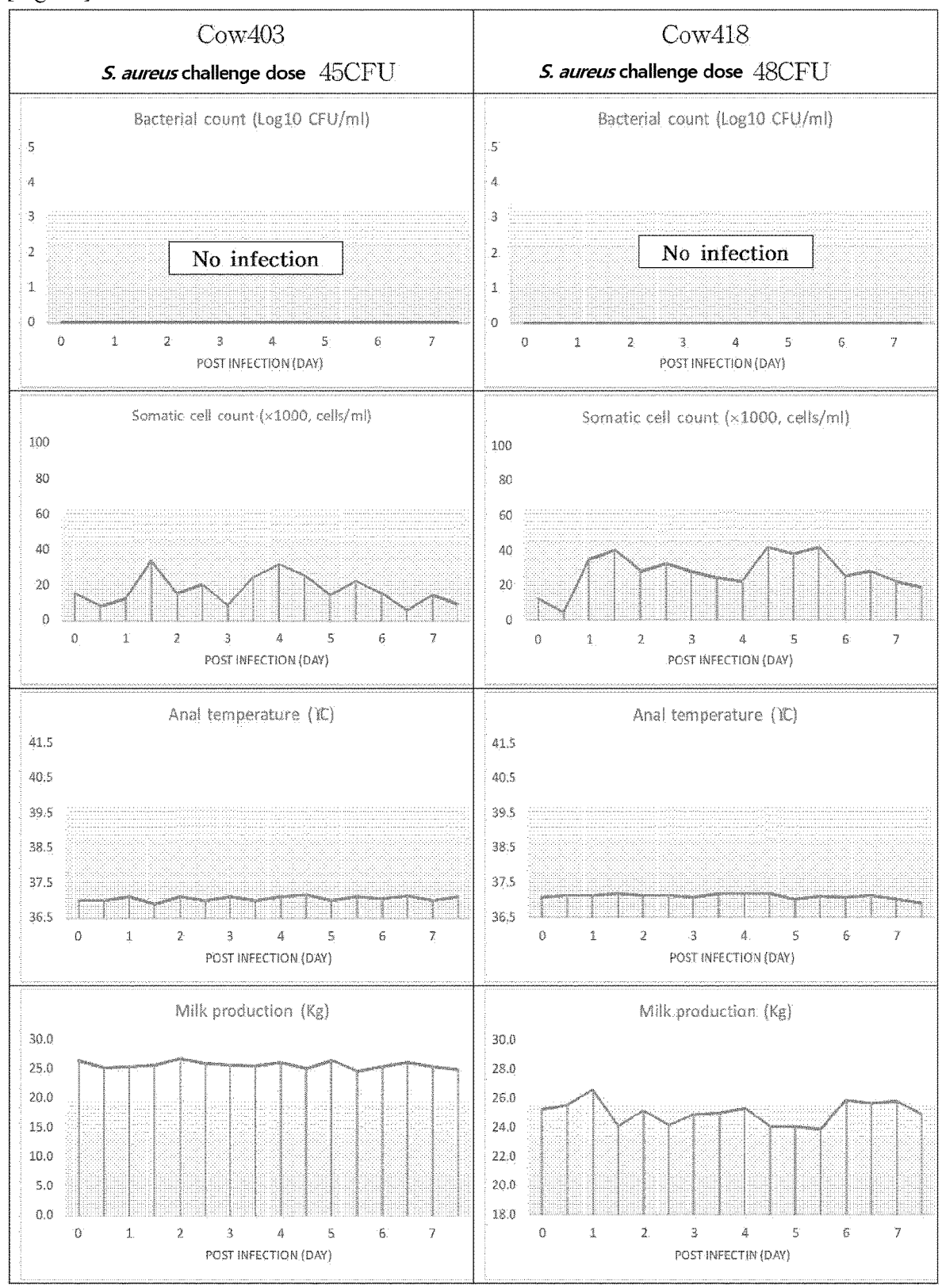

[Fig. 6b]
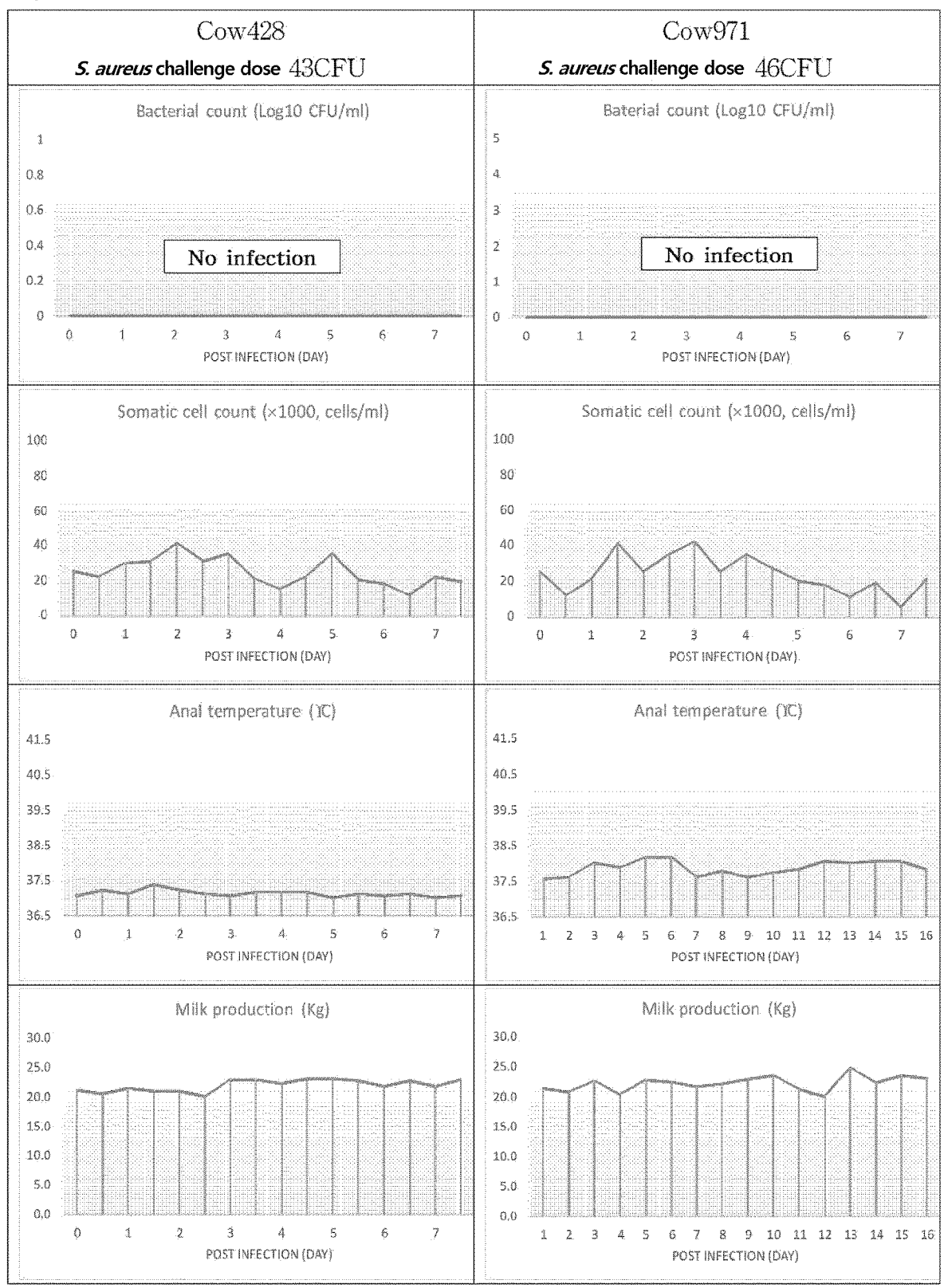

[Fig. 7a]
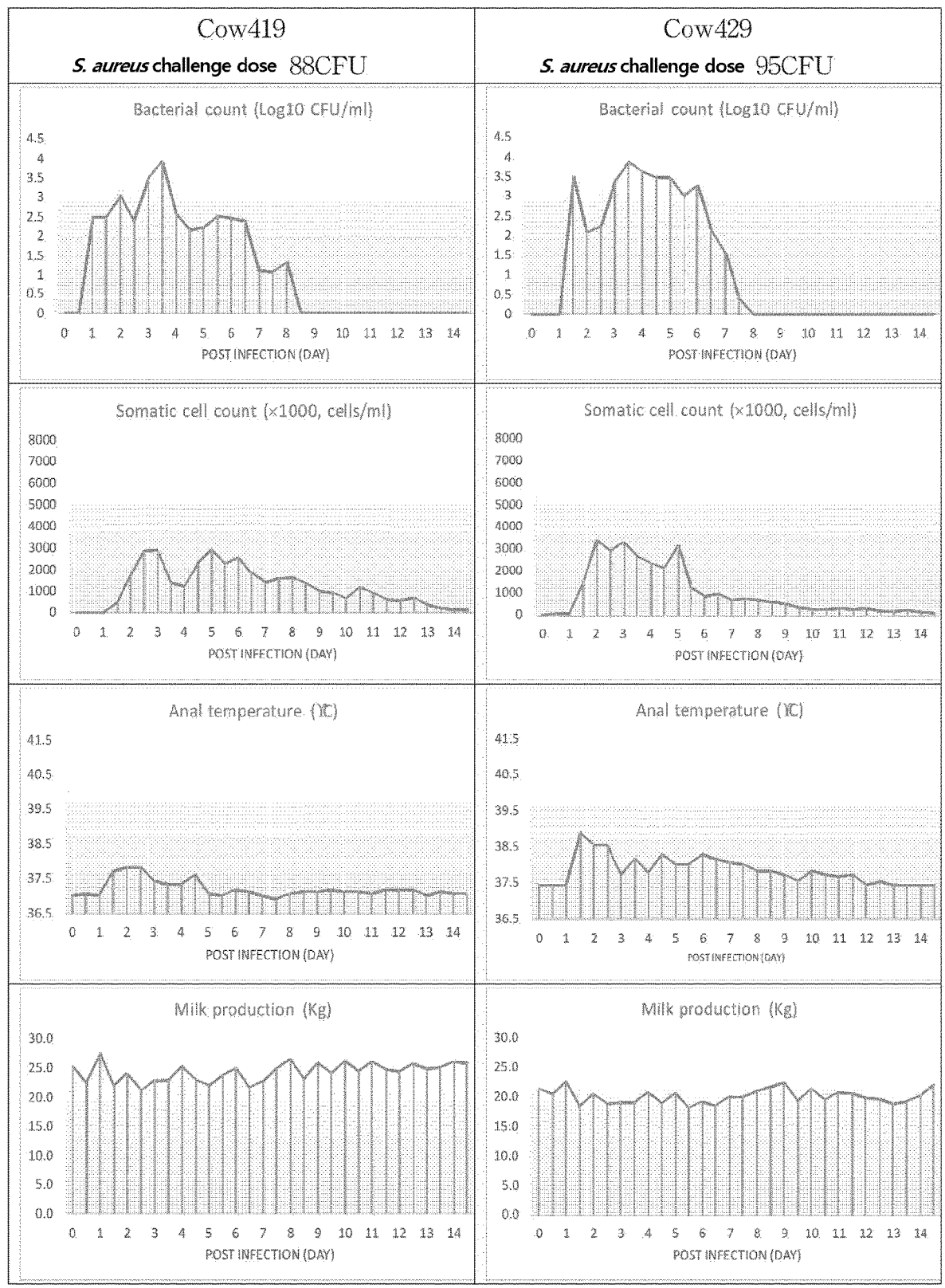

[Fig. 7b]
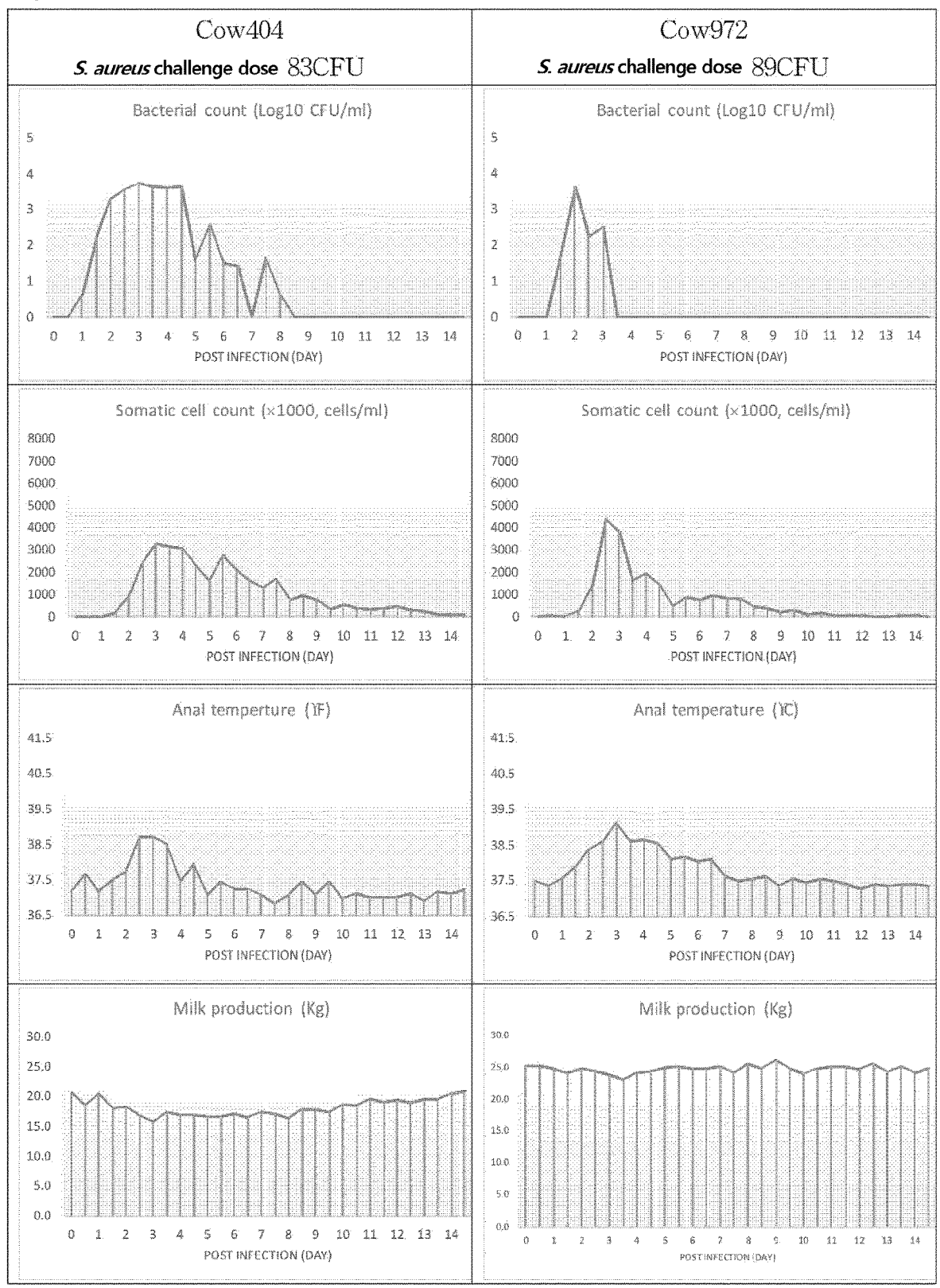

[Fig. 8]
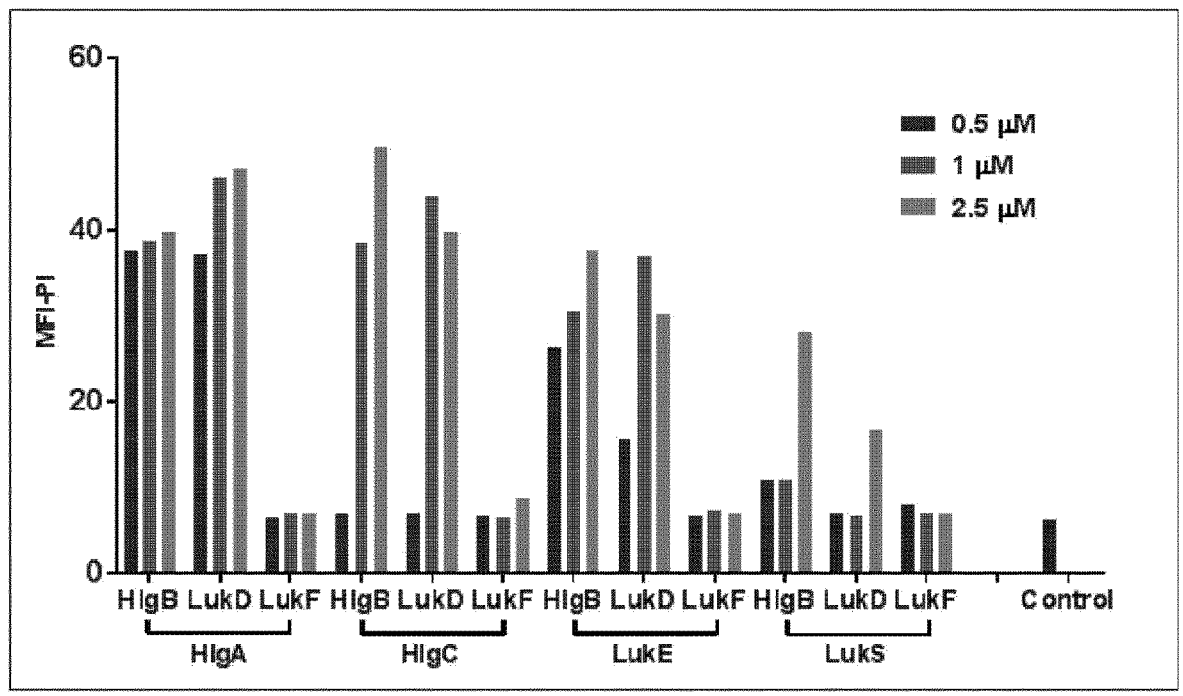
[Fig. 9]
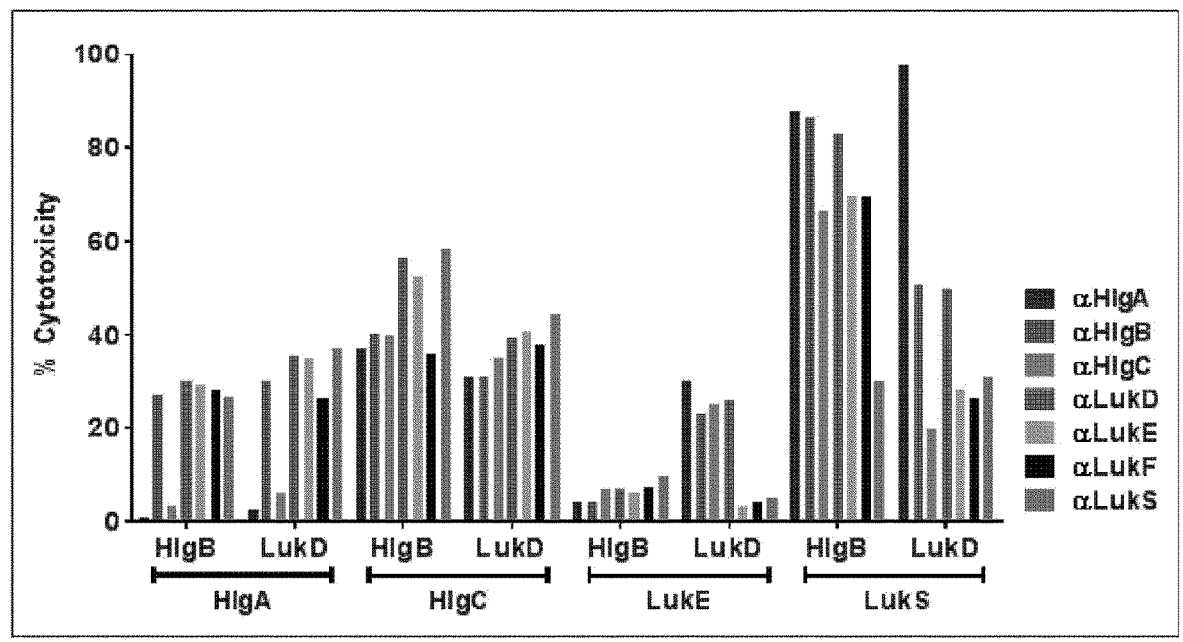

[Fig. 10]
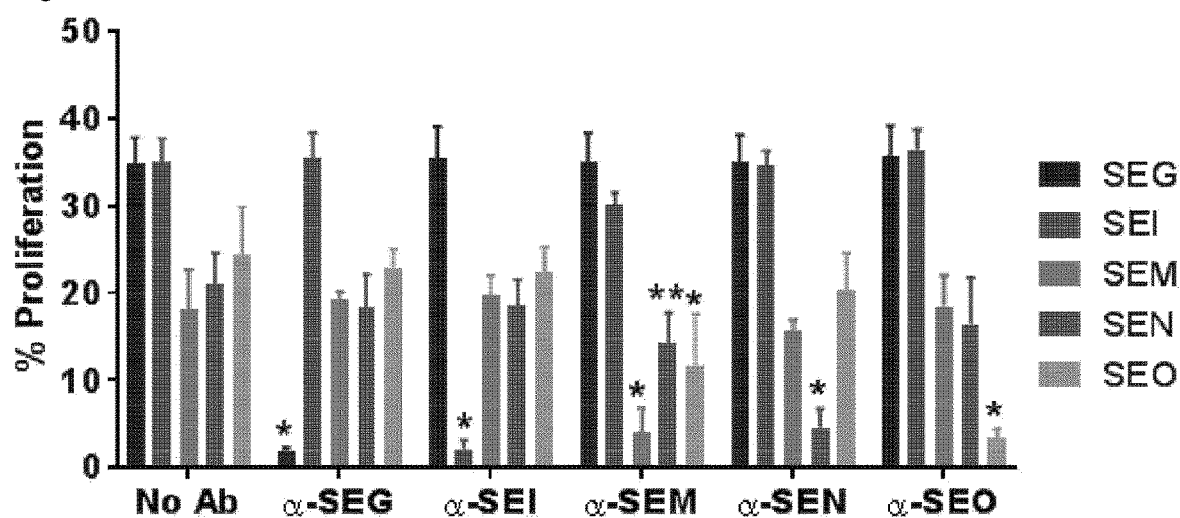

[Fig. 11]
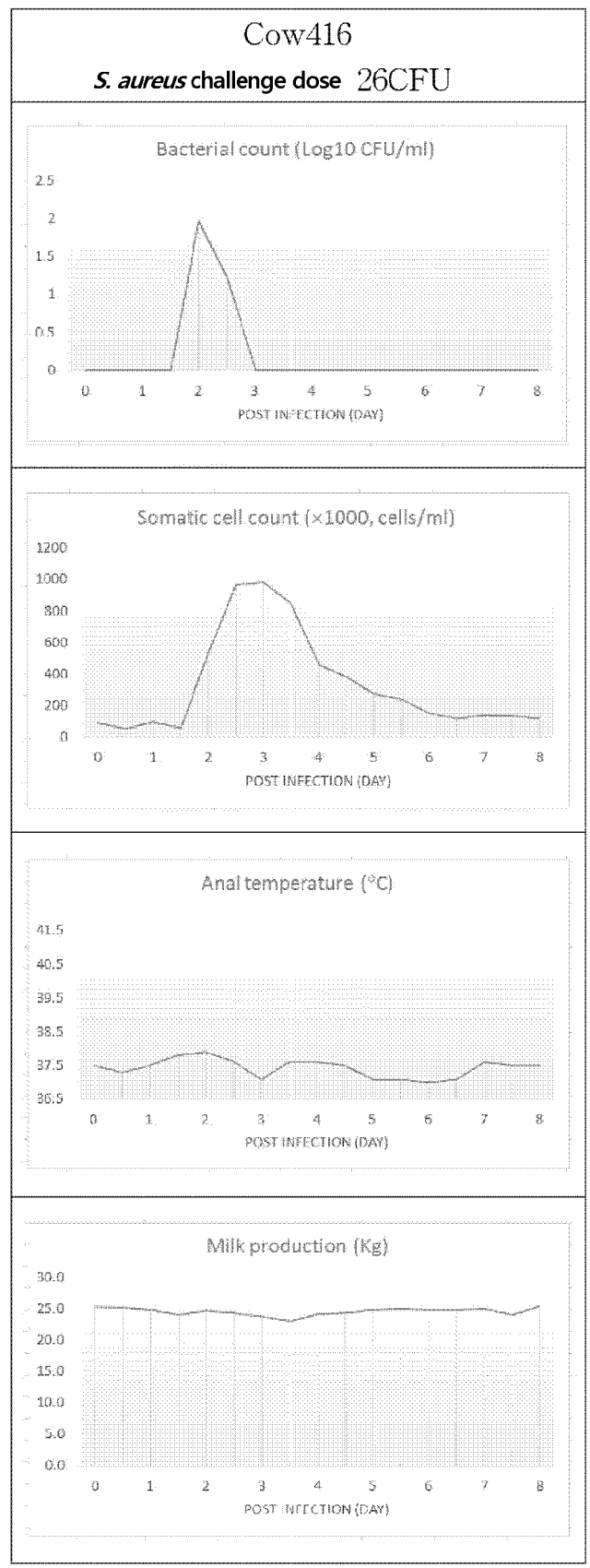

VACCINE COMPOSITION COMPRISING RECOMBINANT PROTEIN OF *STAPHYLOCOCCUS AUREUS* ATTENUATED ENTEROTOXIN AND CYTOTOXIN

CROSS-REFERENCE TO RELATED APPLICATIONS

This application is a national stage application filed under 35 U.S.C. § 371 of International Patent Application No. PCT/KR2018/015865, filed Dec. 13, 2018, which claims the benefit of KR 10-2018-0066226 filed Jun. 8, 2018.

INCORPORATION OF MATERIAL OF ASCII TEXT SEQUENCE LISTING BY REFERENCE

The sequence listing submitted herewith as a text file named "MSU-1008US_Substitute Sequence Listing" created on Feb. 5, 2021, which is 39,000 bytes in size, is hereby incorporated by reference in its entirety.

TECHNICAL FIELD

The present invention relates to a vaccine composition comprising *Staphylococcus aureus* attenuated enterotoxin protein and cytotoxic protein, and more particularly to *Staphylococcus aureus* enterotoxin protein, *Staphylococcus aureus* cytotoxin protein, a vaccine composition for preventing bovine mastitis, comprising the *Staphylococcus aureus* enterotoxin protein and *Staphylococcus aureus* cytotoxin protein and a method for preventing bovine mastitis comprising administering the vaccine composition to a bovine.

BACKGROUND

Bovine mastitis directly affects milk quality and milk production so that it is a disease which the most economically damages to the dairy industry. *Staphylococcus aureus* is the most important etiologic agent among the causative viruses of mastitis. It is difficult to treat with antibiotics due to multiple resistance. After treatment, the prognosis is poor. Therefore, cattle infected with mastitis by *Staphylococcus aureus* are usually recommended to be culled. Accordingly, the prevention through vaccination is the most effective method for the management of *Staphylococcus aureus* mastitis. However, the vaccine currently being developed or developed has been developed on the basis of proteins or capsules present in *Staphylococcus aureus* strain. Hence, there are mutations in these antigens, which do not show any substantial preventive effect. In addition, they do not match with encapsulation type and pathogenic factors having a high frequency in *Staphylococcus aureus* in Korea so that the preventive effect is low. Mastitis caused by *Staphylococcus aureus* occurs due to a result of complicated interactions between pathogenic factors. Mastitis is significantly increased due to enterotoxin and cytotoxin factors produced by *Staphylococcus aureus* so that defense mechanisms for these pathogenic factors are required for effective prevention and treatment of mastitis by *Staphylococcus aureus*.

DESCRIPTION OF DISCLOSURE

Technical Problem

Accordingly, the present inventors have studied effective prevention and treatment of mastitis due to *Staphylococcus aureus*. As a result, the present inventors have developed attenuated enterotoxin and cytotoxin by screening the most frequent pathogenic factors in *Staphylococcus aureus* isolated from bovine mastitis in Korean dairy cattle and confirmed excellent safety and protective ability against challenge test of the vaccine including the same, thereby completing the present invention.

Accordingly, there are objects of this invention to provide a *Staphylococcus aureus* enterotoxin protein, a *Staphylococcus aureus* cytotoxin protein, a recombinant vector including a gene encoding the proteins, a transformant into which the recombinant vector is inserted, a vaccine composition for preventing bovine mastitis, comprising the *Staphylococcus aureus* enterotoxin protein and *Staphylococcus aureus* cytotoxin protein and a method for preventing bovine mastitis, comprising administering the vaccine composition to a bovine.

Technical Solution

To achieve the objects, the present invention is to provide a *Staphylococcus aureus* enterotoxin protein comprising the amino acid sequences represented by SEQ ID NO: 2, SEQ ID NO: 4, SEQ ID NO: 6, SEQ ID NO: 8 or SEQ ID NO: 10.

Further, the present invention is to provide a *Staphylococcus aureus* cytotoxin protein including the amino acid sequences represented by SEQ ID NO: 15, SEQ ID NO: 19, SEQ ID NO: 23 or SEQ ID NO: 27. Further, the present invention is to provide a recombinant vector including a gene encoding the proteins. Further, the present invention is to provide a transformant into where the recombinant vector is inserted. Further, the present invention is to provide a vaccine composition for prevention of bovine mastitis, the composition comprising *Staphylococcus aureus* enterotoxin proteins represented by SEQ ID NO: 2, SEQ ID NO: 4 and SEQ ID NO: 6; and *Staphylococcus aureus* cytotoxin proteins represented by SEQ ID NO: 15, SEQ ID NO: 23 and SEQ ID NO: 27 as an antigen.

Further, the present invention is to provide a method for preventing bovine mastitis, the method comprising administering the vaccine composition for the prevention of bovine mastitis to a bovine.

Advantageous Effects

The *Staphylococcus aureus* enterotoxin protein, *Staphylococcus aureus* cytotoxin protein according to the present invention and vaccine composition containing the proteins as an antigen can be used so that even vaccines containing several antigens rather than all kinds of antigens show the excellent effects of prevention and treatment of bovine mastitis against all kinds of *Staphylococcus aureus* enterotoxin and cytotoxin having high incidence in Korea, thereby being more economically used for industrial purposes. Further, the vaccine composition for prevention of bovine mastitis, comprising the *Staphylococcus aureus* enterotoxin protein and *Staphylococcus aureus* cytotoxin protein according to the present invention has an excellent safety and bovine mastitis prevention and treatment effect even in the high CFU *Staphylococcus aureus* challenge test so that the composition can be variously utilized in *Staphylococcus aureus* vaccine and prevention related fields in future.

BRIEF DESCRIPTION OF DRAWINGS

FIG. 1 is a view of illustrating the results of chromatographic analysis of purified attenuated enterotoxin and cytotoxin recombinant proteins of the present invention.

FIG. 2 is a view of illustrating the results of examining the survival rate by mouse challenge test on the only PBS-inoculated control group, the only present invention's enterotoxin protein-inoculated group, the only present invention's cytotoxin protein-inoculated group, and the present invention's mixture with enterotoxin and cytotoxin-inoculated group in order to confirm effectiveness of antigens.

FIG. 3 is a view of illustrating changes in IgG antibody according to the amount of antigen to determine the amount of antigen that induces an optimal antibody reaction.

FIG. 4 is a view of illustrating the results of measuring the somatic cell count and milk production in the vaccine-inoculated group and the control group to confirm the vaccine safety of the present invention.

FIG. 5 is a view of illustrating the results of measuring changes in the bacterial count, somatic cell count, temperature and milk production to indicate clinical symptoms after 4 to 10 CFU of Staphylococcus aureus (K30) challenge test on the control group (PBS+aluminum hydroxide gel) in order to compare with the effect of preventing the mastitis of the present invention's vaccine.

FIG. 6 includes views of illustrating the results of measuring changes in the bacterial count, somatic cell count, temperature and milk production to indicate clinical symptoms after 43 to 48 CFU of Staphylococcus aureus (K30) challenge test on the vaccine groups (100 μg of each attenuated enterotoxin+100 μg of each attenuated cytotoxin+aluminum hydroxide gel) in order to compare with the effect of preventing the mastitis of the present invention's vaccine in which FIG. 6A illustrates the results for 45 and 48 CFU and FIG. 6B illustrates the results for 43 and 46 CFU.

FIG. 7 includes views of illustrating the results of measuring changes in the bacterial count, somatic cell count, temperature and milk production to indicate clinical symptoms after 83 to 95 CFU of Staphylococcus aureus (K30) challenge test on the vaccine groups in order to compare with the effect of preventing the mastitis of the present invention's vaccine in which FIG. 7A illustrates the results for 88 and 95 CFU and FIG. 7B illustrates the results for 83 and 89 CFU.

FIG. 8 is a view of illustrating the results, by flow cytometry, of measuring a degree of intracellular penetration of propidium iodide on Bovine Leukocyte as a control group according to antigen combination of 7 kinds of cytotoxins (HgA, HlgB, HlgC, LukD, LukE, LukF and LukS) before confirming the cross-neutralizing ability of the antigen of the present invention.

FIG. 9 is a view of illustrating the results of measuring cytotoxin neutralizing ability using a neutralizing antibody in order to confirm the cross-neutralizing ability of the cytotoxin protein antigen of the present invention.

FIG. 10 is a view of illustrating the results of measuring enterotoxin neutralizing ability using a neutralizing antibody in order to confirm the cross-neutralizing ability of the enterotoxin protein antigen of the present invention.

FIG. 11 is a view of illustrating the results of measuring changes in the bacterial count, somatic cell count, temperature and milk production amount to indicate clinical symptoms after 26 CFU of Staphylococcus aureus (K30) challenge test on the vaccine groups in order to confirm preventive effect of mastitis by vaccines including 3 kinds of cytotoxins and 3 kinds of enterotoxins (HgA, LukE, LukS, SEG, SEI, SEM) having neutralizing ability of the present invention.

BEST MODE

The present invention provides a Staphylococcus aureus enterotoxin protein comprising the amino acid sequences represented by SEQ ID NO: 2, SEQ ID NO: 4, SEQ ID NO: 6, SEQ ID NO: 8 or SEQ ID NO: 10.

Staphylococcus aureus of the present invention is a microorganism, which is referred to as "Staphylococcus aureus," "Staph," "Staph. aureus" or "S. aureus." In addition, Staphylococcus aureus is one of the important causative bacteria of bovine mastitis and is one of the bacteria that is highly noted in the veterinary field. Further, Staphylococcus aureus of the present invention may be preferably a microorganism isolated from raw milk samples of dairy cattle with mastitis.

Further, the amino acid sequence represented by SEQ ID NO: 2 may be derived from Staphylococcus aureus enterotoxin SEG, the amino acid sequence represented by SEQ ID NO: 4 may be derived from Staphylococcus aureus enterotoxin SEI, the amino acid sequence represented by SEQ ID NO: 6 may be derived from Staphylococcus aureus enterotoxin SEM, the amino acid sequence represented by SEQ ID NO: 8 may be derived from Staphylococcus aureus enterotoxin SEN, and the amino acid sequence represented by SEQ ID NO: 10 may be derived from Staphylococcus aureus enterotoxin SEO. The Staphylococcus aureus enterotoxins SEG, SEI, SEM, SEN, and SEO are ones that have a high frequency of occurrence in Korea.

The Staphylococcus aureus enterotoxin protein of the present invention may preferably be an attenuated recombinant protein. Further, the Staphylococcus aureus enterotoxin protein of the present invention may include all polypeptides having a homology of 70% or more, preferably 80% or more, more preferably 90% or more, and most preferably 95% or more with amino acid sequences represented by SEQ ID NO: 2, SEQ ID NO: 4, SEQ ID NO: 6, SEQ ID NO: 8 or SEQ ID NO: 10, respectively. "Homology" refers to a measure of the similarity between proteins or polypeptide sequences. These polypeptides may include deletion, addition or substitution of at least one amino acid compared to the amino acid sequences represented by SEQ ID NO: 2, SEQ ID NO: 4, SEQ ID NO: 6, SEQ ID NO: 8 or SEQ ID NO: 10. The degree of homology between two sequences is scored, which is based on preserving the percentage of identities and/or substitutions of the sequence.

The Staphylococcus aureus enterotoxin protein can be isolated using conventional protein separation methods. For example, the Staphylococcus aureus enterotoxin protein can be isolated by methods including, but not limited to, centrifugation, filtration, extraction, spray drying, evaporation or precipitation. Furthermore, the Staphylococcus aureus enterotoxin protein can be purified by known methods including chromatography (e.g., ion exchange, affinity, hydrophobicity and size exclusion), electrophoresis, differential solubility (e.g., ammonium sulfate precipitation), SDS-PAGE or extraction.

The amino acid sequence represented by SEQ ID NO: 2 may be encoded by the nucleotide sequence represented by SEQ ID NO: 1, the amino acid sequence represented by SEQ ID NO: 4 may be encoded by the nucleotide sequence represented by SEQ ID NO: 3, the amino acid sequence represented by SEQ ID NO: 6 may be encoded by the nucleotide sequence represented by SEQ ID NO: 5, the amino acid sequence represented by SEQ ID NO: 8 may be encoded by the nucleotide sequence represented by SEQ ID NO: 7, and the amino acid sequence represented by SEQ ID NO: 10 may be encoded by the nucleotide sequence represented by SEQ ID NO: 9, but the present invention is not limited thereto.

Further, the nucleotide sequence or gene represented by SEQ ID NO: 1, SEQ ID NO: 3, SEQ ID NO: 5, SEQ ID NO:

7 or SEQ ID NO: 9 can be synthesized artificially using a nucleic acid synthesizer or the like with reference to the nucleotide sequence of the corresponding gene or can be synthesized by performing PCR using *Staphylococcus aureus* genomic DNA or each gene as a template and an oligonucleotide sequence having a sequence complementary to both ends of the desired nucleotide sequence or gene as a primer. Meanwhile, due to codon degeneracy, the nucleotide sequence or gene of the present invention may present in various nucleotide sequences. All of them fall within the scope of the present invention. Further, the variants of the nucleotide sequence or gene represented by SEQ ID NO: 1, SEQ ID NO: 3, SEQ ID NO: 5, SEQ ID NO: 7 or SEQ ID No 9 fall within the scope of the present invention. Specifically, the nucleotide sequence or gene of the present invention may have a sequence homology of 70% or more, preferably 80% or more, more preferably 90% or more, and most preferably 95% or more with nucleotide sequences represented by SEQ ID NO: 1, SEQ ID NO: 3, SEQ ID NO: 5, SEQ ID NO: 7 or SEQ ID NO: 9, respectively. "Sequence homology %" for the nucleotide sequence may be identified by comparing the comparison regions and two optimally arranged sequences. A portion of the nucleotide sequence in the comparison region may include addition or deletion (i.e., gap) compared to the reference sequence (excluding addition or deletion) for optimal arrangement of the two sequences.

Further, the amino acid sequences represented by SEQ ID NO: 2, SEQ ID NO: 4, SEQ ID NO: 6, SEQ ID NO: 8 and SEQ ID NO: 10 may be sequences that histidine and aspartic acid which are MHC class II binding site amino acids are substituted with alanine. The above-mentioned "substitution" can be performed preferably through overlap PCR, but is not limited thereto. By substituting as described above, the *Staphylococcus aureus* enterotoxin of the present invention may be attenuated by inhibiting binding with strong binding force to MHC class II.

The *Staphylococcus aureus* enterotoxin protein of the present invention may be used as an antigen in a vaccine composition to neutralize all 5 kinds of antigens, *Staphylococcus aureus* enterotoxins (SEG, SEI, SEM, SEN and SEO), which can effectively prevent and treat mastitis mainly caused by *Staphylococcus aureus* in a bovine.

Further, the present invention provides a method for preventing bovine mastitis, the method comprising: administering the *Staphylococcus aureus* enterotoxin protein comprising the amino acid represented by SEQ ID NO: 2, SEQ ID NO: 4, SEQ ID NO: 6, SEQ ID NO: 8 or SEQ ID NO: 10 to an individual.

Further, the present invention provides a *Staphylococcus aureus* cytotoxin protein comprising the amino acid represented by SEQ ID NO: 15, SEQ ID NO: 19, SEQ ID NO: 23 or SEQ ID NO: 27.

The amino acid sequence represented by SEQ ID NO: 15 may be derived from *Staphylococcus aureus* cytotoxin HlgA, the amino acid sequence represented by SEQ ID NO: 19 may be derived from *Staphylococcus aureus* cytotoxin HlgC, the amino acid sequence represented by SEQ ID NO: 23 may be derived from *Staphylococcus aureus* cytotoxin LukE, and the amino acid sequence represented by SEQ ID NO: 27 may be derived from *Staphylococcus aureus* cytotoxin LukS. The *Staphylococcus aureus* cytotoxins HlgA, HlgC, LukE and LukS are ones that have a high frequency of occurrence in Korea.

The *Staphylococcus aureus* cytotoxin protein of the present invention may preferably be an attenuated recombinant protein. Further, the *Staphylococcus aureus* cytotoxin protein of the present invention may include all polypeptides having a homology of 70% or more, preferably 80% or more, more preferably 90% or more, and most preferably 95% or more with amino acid sequences represented by SEQ ID NO: 15, SEQ ID NO: 19, SEQ ID NO: 23 or SEQ ID NO: 27, respectively. "Homology" refers to a measure of the similarity between proteins or polypeptide sequences. These polypeptides may include deletion, addition or substitution of at least one amino acid compared to the amino acid sequences represented by SEQ ID NO: 15, SEQ ID NO: 19, SEQ ID NO: 23 or SEQ ID NO: 27. The degree of homology between two sequences is scored, which is based on preserving the percentage of identities and/or substitutions of the sequence.

The *Staphylococcus aureus* cytotoxin protein can be isolated using conventional protein separation methods. For example, *Staphylococcus aureus* cytotoxin protein can be isolated by methods including, but not limited to, centrifugation, filtration, extraction, spray drying, evaporation or precipitation. Furthermore, the *Staphylococcus aureus* enterotoxin protein and *Staphylococcus aureus* cytotoxin protein can be purified by known methods including chromatography (e.g., ion exchange, affinity, hydrophobicity and size exclusion), electrophoresis, differential solubility (e.g., ammonium sulfate precipitation), SDS-PAGE or extraction. Further, the amino acid sequence represented by SEQ ID NO: 15 may be a sequence in which AXA motif is cleaved after being encoded by the nucleotide sequence represented by SEQ ID NO: 14, the amino acid sequence represented by SEQ ID NO: 19 may be a sequence in which AXA motif is cleaved after being encoded by the nucleotide sequence represented by SEQ ID NO: 18, the amino acid sequence represented by SEQ ID NO: 23 may be a sequence in which AXA motif is cleaved after being encoded by the nucleotide sequence represented by SEQ ID NO: 22, and the amino acid sequence represented by SEQ ID NO: 27 may be a sequence in which AXA motif is cleaved after being encoded by the nucleotide sequence represented by SEQ ID NO: 26. The nucleotide sequence represented by SEQ ID NO: 14 may be a sequence comprising nucleotide sequences represented by SEQ ID NO: 11, SEQ ID NO: 12 and SEQ ID NO: 13. The nucleotide sequence represented by SEQ ID NO: 18 may be a sequence comprising nucleotide sequences represented by SEQ ID NO: 11, SEQ ID NO: 16 and SEQ ID NO: 17. The nucleotide sequence represented by SEQ ID NO: 22 may be a sequence comprising nucleotide sequences represented by SEQ ID NO: 11, SEQ ID NO: 20 and SEQ ID NO: 21. The nucleotide sequence represented by SEQ ID NO: 26 may be a sequence comprising nucleotide sequences represented by SEQ ID NO: 11, SEQ ID NO: 24 and SEQ ID NO: 25. Further, the nucleotide sequence represented by SEQ ID NO: 11 may be a nucleotide sequence of ETA promoter (exfoliative toxin A promoter). The nucleotide sequences represented by SEQ ID NO: 12, by SEQ ID NO: 16, SEQ ID NO: 20 and SEQ ID NO: 24 may be nucleotide sequences of signal peptides. The nucleotide sequences represented by SEQ ID NO: 13, by SEQ ID NO: 17, SEQ ID NO: 21 and SEQ ID NO: 25 may be nucleotide sequences of mature proteins. The ETA promoter may be a Staphylococcal exfoliative toxin A promoter (ETA promoter) of a *Staphylococcus aureus* strain LAC strain. The nucleotide sequences of the ETA promoter, signal peptide and mature protein may be linked to efficiently purify the secreted *Staphylococcus aureus* cytotoxin which is encoded.

Further, the amino acid sequence represented by SEQ ID NO: 15 may be encoded by the nucleotide sequence represented by SEQ ID NO: 13, the amino acid sequence represented by SEQ ID NO: 19 may be encoded by the nucleotide sequence represented by SEQ ID NO: 17, the amino acid sequence represented by SEQ ID NO: 23 may be encoded by the nucleotide sequence represented by SEQ ID NO: 21, and the amino acid sequence represented by SEQ ID NO: 27 may be encoded by the nucleotide sequence represented by SEQ ID NO: 25, but is not limited thereto.

Further, the nucleotide sequence or gene represented by SEQ ID NOs: 11 to 14, SEQ ID NOs: 16 to 18, SEQ ID NOs: 20 to 22 and SEQ ID NOs: 24 to 26 can be synthesized artificially using a nucleic acid synthesizer or the like with reference to the nucleotide sequence of the corresponding gene or can be synthesized by performing PCR using *Staphylococcus aureus* genomic DNA or each gene as a template and an oligonucleotide sequence having a sequence complementary to both ends of the desired nucleotide sequence or gene as a primer. Meanwhile, due to codon degeneracy, the nucleotide sequence or gene of the present invention may present in various nucleotide sequences. All of them fall within the scope of the present invention. Further, the variants of the nucleotide sequence or gene represented by SEQ ID NOs: 11 to 14, SEQ ID NOs: 16 to 18, SEQ ID NOs: 20 to 22 and SEQ ID NOs: 24 to 26 fall within the scope of the present invention. Specifically, the nucleotide sequence or gene of the present invention may have a sequence homology of 70% or more, preferably 80% or more, more preferably 90% or more, and most preferably 95% or more with nucleotide sequences represented by SEQ ID NOs: 11 to 14, SEQ ID NOs: 16 to 18, SEQ ID NOs: 20 to 22 and SEQ ID NOs: 24 to 26, respectively. "Sequence homology %" for the nucleotide sequence may be identified by comparing the comparison regions and two optimally arranged sequences. A portion of the nucleotide sequence in the comparison region may include addition or deletion (i.e., gap) compared to the reference sequence (excluding addition or deletion) for optimal arrangement of the two sequences.

The *Staphylococcus aureus* cytotoxin protein of the present invention may be used as an antigen in a vaccine composition to neutralize all 7 kinds of antigens, *Staphylococcus aureus* cytotoxins (HgA, HlgB, HlgC, LukD, LukE, LukF and LukS), which can effectively prevent and treat mastitis mainly caused by *Staphylococcus aureus* in a bovine.

Further, the present invention provides a method for preventing or treating bovine mastitis, the method comprising: administering the *Staphylococcus aureus* cytotoxin protein comprising the amino acid represented by SEQ ID NO: 15, SEQ ID NO: 19, SEQ ID NO: 23 or SEQ ID NO: 27 to an individual.

Further, the present invention provides a recombinant vector comprising a gene encoding the *Staphylococcus aureus* enterotoxin protein or the *Staphylococcus aureus* cytotoxin protein.

In the present invention, the term "vector" refers to a plasmid, virus or other mediators known in the art to which a gene or nucleotide sequence can be inserted or introduced. The nucleotide sequence according to the present invention may be operably linked to an expression control sequence and the operably linked nucleotide sequence may be included within an expression vector including a selection marker and a replication origin. The term "operably linked" may refer to a gene and expression control sequence linked in such a scheme to enable expression of the gene when the appropriate molecule is linked to the expression control sequence. The "expression control sequence" means a DNA sequence that controls the expression of a nucleotide sequence operably linked to a particular host cell. Such a control sequence includes a promoter for conducting transcription, any operator sequence for controlling transcription, a sequence encoding suitable mRNA ribosome binding sites, and a sequence controlling the termination of transcription and translation.

Further, the present invention provides a transformant into which the recombinant vector is inserted.

In the present invention, the term "transformation" refers to changes in the genetic properties of an organism due to exogenously given DNA, and the term "transformant" of the present invention refers to the transformation of a transgenic plant or transgenic animal caused by transformation and includes a genetic recombinant produced by inducing a modification or mutation of a specific gene using a gene recombination technique. The transformant of the present invention may be *Staphylococcus aureus* RN4220 strain or *Escherichia coli* BL21 strain, but is not limited thereto.

Further, the present invention provides a vaccine composition for prevention of bovine mastitis, comprising *Staphylococcus aureus* enterotoxin proteins represented by SEQ ID NO: 2, SEQ ID NO: 4 and SEQ ID NO: 6 and *Staphylococcus aureus* cytotoxin proteins represented by SEQ ID NO: 15, SEQ ID NO: 23 and SEQ ID NO: 27 as an antigen.

The term "bovine mastitis" in the present invention is preferably mastitis occurring in the dairy cattle, which is a disease in which inflammation of the mammary gland is caused by various microbial infections distributed in nature. Further, there are symptoms such as a decrease in milk production, a decrease of milk quality, fever and loss of appetite depending on the degree of symptoms. In severe cases, it is not only a loss of dairy cattle function but also infectious to be at risk of being killed. Reduced quantity and quality of milk due to mastitis are directly related to the economic loss of dairy farmers. In particular, it is more meaningful under the conventional system in which the milk price depends on the milk quality.

In the present invention, the term "prevention" refers to any action that inhibits the symptoms of bovine mastitis or delays the onset of mastitis by administration of a composition. In the present invention, the term "vaccine" refers to an antigen used to automatically immunize a human or an animal as the prevention of an infectious disease. In the present invention, the vaccine preferably refers to an immunogen that causes an immune response by inserting or injecting it into an organism so as to prevent bovine mastitis. Further, the vaccine of the present invention may be an attenuated live vaccine, inactivated vaccine, killed vaccine, subunit vaccine, synthetic vaccine or genetic engineering vaccine, but preferably is a genetic engineering vaccine.

*Staphylococcus aureus* enterotoxin proteins represented by SEQ ID NO: 2, SEQ ID NO: 4 and SEQ ID NO: 6, respectively, are derived from *Staphylococcus aureus* enterotoxin SEG, SEI and SEM and are the *Staphylococcus aureus* enterotoxin proteins produced in the present invention. *Staphylococcus aureus* cytotoxin proteins represented by SEQ ID NO: 15, SEQ ID NO: 23 and SEQ ID NO: 27, respectively, are derived from *Staphylococcus aureus* cytotoxin HlgA, LukE and LukS and are the *Staphylococcus aureus* cytotoxin proteins produced in the present invention. The vaccine composition for prevention of bovine mastitis comprising the *Staphylococcus aureus* enterotoxin proteins represented by SEQ ID NO: 2, SEQ ID NO: 4 and SEQ ID NO: 6 and the *Staphylococcus aureus* cytotoxin proteins represented by SEQ ID NO: 15, SEQ ID NO: 23 and SEQ ID NO: 27 as an antigen is used to neutralize all 5 kinds of antigens, *Staphylococcus aureus* enterotoxins (SEG, SEI, SEM, SEN and SEO) as well as *Staphylococcus aureus* enterotoxin SEG, SEI and SEM. Further, it may neutralize all 7 kinds of antigens, *Staphylococcus aureus* cytotoxins (HlgA, HlgB, HlgC, LukD, LukE, LukF and LukS) as well as *Staphylococcus aureus* cytotoxin HlgA, LukE and LukS.

Accordingly, the vaccine composition for prevention of bovine mastitis of the present invention can be used so that even vaccines containing several antigens rather than all kinds of antigens show the excellent effects of prevention and treatment of bovine mastitis against all kinds of *Staphylococcus aureus* enterotoxin and cytotoxin having high incidence in Korea, thereby being more economically used for industrial purposes. The vaccine composition for prevention of bovine mastitis may further include *Staphylococcus aureus* enterotoxin proteins represented by SEQ ID NO: 8 and SEQ ID NO: 10. The *Staphylococcus aureus* enterotoxin proteins represented by SEQ ID NO: 8 and SEQ ID NO: 10 are derived from *Staphylococcus aureus* enterotoxin SEN and SEO, respectively, and prepared in the present invention. The vaccine composition for prevention of bovine mastitis may further include a *Staphylococcus aureus* cytotoxin protein represented by SEQ ID NO: 19. The *Staphylococcus aureus* cytotoxin protein represented by SEQ ID NO: 19 is derived from *Staphylococcus aureus* cytotoxin HlgC and is a *Staphylococcus aureus* cytotoxin protein prepared in the present invention. The *Staphylococcus aureus* enterotoxin protein or *Staphylococcus aureus* cytotoxin protein represented by the sequence number may be added to further maximize the effect of preventing and treating bovine mastitis.

Further, the *Staphylococcus aureus* enterotoxin protein and the *Staphylococcus aureus* cytotoxin protein may be included in a weight of 50 μg to 200 μg, preferably 50 μg to 150 μg, more preferably 50 μg to 100 μg. Such an antigen amount may induce the optimal antibody reaction of the vaccine composition.

Further, in the present invention, the vaccine composition may further include an adjuvant. The adjuvant is a substance that promotes an immune response to an antigen nonspecifically in the initial activation process of immune cells. The adjuvant that may be administered together with the composition of the present invention to improve the immune response includes any of various adjuvants. The adjuvant may be administered simultaneously with the vaccine composition or sequentially administered at intervals of time. In the present invention, ISA70, aluminum hydroxide gel, Freund's incomplete or complete adjuvant, aluminum hydroxide gel and vegetable and mineral oil are used as adjuvants. Preferably, the vaccine composition of the present invention may further include, but is not limited to, aluminum hydroxide gel.

In the present invention, the vaccine composition may further include at least one kind selected from the group consisting of a solvent and an excipient in addition to the adjuvant. The solvent may be physiological saline or distilled water, and the excipient may be aluminum phosphate, aluminum hydroxide or aluminum potassium sulfate, but not limited thereto. Further, if the substance is used to prepare vaccine well known by those skilled in the art, it can be included without limitation, as long as it does not inhibit the action of the vaccine of the present invention.

In the present invention, the vaccine composition may be prepared as an oral or parenteral formulation, preferably prepared as an injectable solution which is a parenteral formulation. It can be administered via dermis, intramuscular, intraperitoneal, intravenous, nasal, epidural, or other appropriate routes. Preferably, it may be prepared as an intramuscular injection to be administered intramuscularly, but is not limited thereto.

In the present invention, the vaccine composition may be administered to an animal in the form of carrier-bound or by a method of mixing with feed or drinking water of livestock. In general, a suitable carrier for the vaccine is well known to those skilled in the art, and it includes, but is not limited to, proteins, sugars, etc. In the present invention, the carrier may be an aqueous solution, non-aqueous solution, a suspension or an emulsion.

Examples of the non-aqueous carrier include propylene glycol, polyethylene glycol, vegetable oil such as olive oil and injectable organic ester such as ethyl oleate. The aqueous carrier includes water, an alcohol/aqueous solution, an emulsion or a suspension, including saline and buffered media. The parenteral carrier includes sodium chloride solution, Ringer's dextrose, dextrose and sodium chloride, Ringer of lactic acid treatment or fixed oils. The intravenous carrier includes an electrolyte supplement, liquid and nutritional supplement, such as those based on Ringer's dextrose. Preservatives and other additives such as an antimicrobial agent, an antioxidant, a chelating agent, an inert gas and the like may be additionally contained. Preferred preservatives include formalin, thiomersal, neomycin, polymyxin B and amphotericin B. Further, the vaccine according to the present invention may include one or more suitable emulsifying agents, for example, Span or Tween.

Further, the present invention provides a method for preventing bovine mastitis, the method comprising administering the vaccine composition for the prevention of bovine mastitis to a bovine.

In the present invention, in order to prevent bovine mastitis, the vaccine composition may be administered to a subject in need thereof in a "pharmaceutically effective amount." The subject may mean an animal, preferably livestock, more preferably a bovine in the present invention. The term "pharmaceutically effective amount" means an amount sufficient to treat a disease at a reasonable benefit/risk ratio which is applicable to medical treatment. The effective amount level may depend on the species and severity of the subject, age, gender, the type of infected microorganism/virus, the activity of the drug, the sensitivity to the drug, the administration time, the administration route, the release rate, the treatment duration, factors including co-administered drugs, and other factors well known in the medical arts.

According to the method for preventing bovine mastitis, the method comprising: administering the vaccine composition for prevention of bovine mastitis of the present invention, it can effectively prevent bovine mastitis against all kinds of *Staphylococcus aureus* enterotoxin and cytotoxin which have a high incidence in Korea.

Hereinafter, the present invention is described in more detail based on Examples. It will be apparent by those skilled in the art that Examples are only for describing the present invention in more detail and that the scope of the present invention is not limited by these Examples in accordance with the gist of the present invention.

Example 1. Isolation and Typing of *Staphylococcus aureus*

A total of 766 raw milk samples from dairy cattle with mastitis collected from Gyeonggi-do, Chungcheongbuk-do and Chungcheongnam-do provinces were smeared on blood agar plates to isolate 207 *Staphylococcus aureus*. Spa typing was used for type analysis of isolated *Staphylococcus aureus*. Spa typing is a method that can be used to confirm whether various types of *Staphylococcus aureus* have been collected by typing using the sequence difference of Staphylococcal protein A that *Staphylococcus aureus* has in common. The distribution of spa type and clonal complexes of *Staphylococcus aureus* derived from raw milk from Korean dairy cattle with mastitis confirmed by the above method are shown in Tables 1 and 2, respectively.

TABLE 1

| Clonal complex[a] (No. isolates, %) | spa typing | No. of isolate(%) |
|---|---|---|
| CC1-ST1(22, 10.6%) | t127 | 15(7.2) |
| | t174 | 3(1.4) |
| | t286 | 4(1.9) |
| CC8-ST8(5, 1.4%) | t008 | 1(0.5) |
| | t304 | 4(1.9) |
| CC20-ST20(18, 8.7%) | t164 | 18(8.7) |
| CC72-ST72(12, 5.8%) | t126 | 4(1.9) |
| | t324 | 7(3.4) |
| | t664 | 1(0.5) |

TABLE 1-continued

| Clonal complex[a] (No. isolates, %) | spa typing | No. of isolate(%) |
|---|---|---|
| CC188-ST188(70, 33.8%) | t189 | 70(33.8) |
| CC398-ST398(11, 5.3%) | t034 | 11(5.3) |
| Others(59, 28.5%) | t2883 | 9(4.3) |
| | t7629 | 9(4.3) |
| | t698 | 7(3.4) |
| | t518 | 5(2.4) |
| | t267 | 4(1.9) |
| | t1991 | 3(1.4) |
| | t519 | 3(1.4) |
| | t5821 | 3(1.4) |
| | t4359 | 2(1.0) |
| | t0128(1), t1234(1), t1858(1), t2441(1), t2849(1), t3563(1), t3855(1), t3887(1), t437(1), t5572(1), t701(1), t855(1), t122(1), t208(1) | 14(6.7) |
| Non typeable(10, 4.8%) | | 10(4.8) |

[a]Clonal complex is based on the association with MLST in the database of Ridom SpaServer.

TABLE 2

| Genes | Total(207) | CC1(n = 22) | CC8(n = 5) | CC20(n = 18) | CC72(n = 12) | CC188(n = 70) | CC398(n = 11) | Others( n = 259) | NT(n = 10) |
|---|---|---|---|---|---|---|---|---|---|
| hla | 188(90.8Y)[a] | 19(84.6) | 4(80) | 18(100) | 10(83.3) | 67(95.7) | 11(100) | 50(84.7) | 9(90) |
| hlb | 118(57.0) | 3(13.6) | 3(60) | 18(100) | 5(41.7) | 38(54.3) | 10(90.9) | 33(55.9) | 8(80) |
| hld | 204(98.4) | 22(100) | 5(100) | 18(100) | 12(100) | 69(98.6) | 11(100) | 58(98.0) | 9(90) |
| hlgA | 189(91.3) | 19(84.6) | 4(80) | 18(100) | 11(91.7) | 67(95.7) | 11(100) | 50(84.7) | 9(90) |
| h1gB | 181(87.4) | 19(84.6) | 4(80) | 18(100) | 11(91.7) | 67(95.7) | 5(45.5)[b] | 49(83.1) | 8(80) |
| hlgC | 188(90.8) | 19(84.6) | 4(80) | 18(100) | 11(91.7) | 67(95.7) | 10(90.9) | 50(84.7) | 9(90) |
| lukA | 187(90.3) | 22(100) | 5(100) | 18(100) | 12(100) | 69(98.6) | 1(9.1)[b] | 51(86.4) | 9(90) |
| lukB | 185(89.4) | 22(100) | 5(100) | 18(100) | 12(100) | 69(98.6) | 1(9.1)[b] | 49(83.1) | 9(90) |
| lukD | 186(89.9) | 22(100) | 5(100) | 16(88.9) | 12(100) | 68(97.1) | 3(27.3)[b] | 52(88.1) | 8(80) |
| lukE | 186(89.9) | 22(100) | 5(100) | 16(88.9) | 12(100) | 68(97.1) | 3(27.3)[b] | 52(88.1) | 8(80) |
| lukF-pv | 1(0.5) | 0(0) | 0(0) | 0(0) | 0(0) | 0(0) | 1(9.1) | 0(0) | 0(0) |
| lukS-pv | 1(0.5) | 0(0) | 0(0) | 0(0) | 0(0) | 0(0) | 1(9.1) | 0(0) | 0(0) |
| lukM | 25(12.1) | 5(22.7) | 1(20) | 2(11.1) | 0(0) | 8(11.4) | 0(0) | 9(15.3) | 0(0) |
| lukF | 4(1.9) | 0(0) | 0(0) | 0(0) | 0(0) | 3(4.3) | 0(0) | 1(1.7) | 0(0) |
| bap | 0(0) | 0(0) | 0(0) | 0(0) | 0(0) | 0(0) | 0(0) | 0(0) | 0(0) |
| clfA | 150(72.5) | 20(90.9) | 5(100) | 18(100) | 12(100) | 37(52.9)[b] | 8(72.7) | 40(67.8) | 10(100) |
| clfB | 178(86.0) | 22(100) | 5(100) | 18(100) | 12(100) | 69(98.6) | 2(18.2)[b] | 45(76.3) | 5(50) |
| ebh | 198(95.7) | 22(100) | 5(100) | 18(100) | 12(100) | 70(100) | 8(72.2) | 55(93.2) | 8(80) |
| emp | 183(88.4) | 22(100) | 5(100) | 17(94.4) | 12(100) | 70(100) | 1(9.1)[b] | 48(81.4) | 8(80) |
| fbpA | 206(99.5) | 22(100) | 5(100) | 18(100) | 12(100) | 70(100) | 11(100) | 58(98.3) | 10(100) |
| fnbA | 128(61.8) | 12(54.5) | 3(60) | 12(66.7) | 11(91.7) | 47(67.1) | 1(9.1)[b] | 35(59.3) | 7(70) |
| fnbB | 178(86.0) | 22(100) | 5(100) | 14(77.8) | 11(91.7) | 69(98.6) | 10(90.9) | 44(74.6) | 3(30) |
| chp | 48(23.2) | 0(0) | 0(0) | 1(5.6) | 5(41.7) | 19(27.1) | 0(0) | 21(35.6) | 1(10) |
| sak | 80(38.6) | 19(86.4) | 1(20) | 1(5.6) | 5(41.7) | 30(42.9) | 0(0) | 21(35.6) | 2(20) |
| scn | 75(36.2) | 19(86.4) | 1(20) | 1(5.6) | 4(33.3) | 28(40) | 0(0) | 19(32.2) | 2(20) |
| Sa3 int | 103(49.8) | 17(77.3) | 2(40) | 6(33.3) | 5(41.7) | 34(48.6) | 1(9.1)[b] | 35(59.3) | 2(20) |
| SaPI5int | 0(0) | 0(0) | 0(0) | 0(0) | 0(0) | 0(0) | 0(0) | 0(0) | 0(0) |
| bsa | 54(26.1) | 22(100) | 5(100) | 1(5.6) | 0(0) | 15(21.4) | 0(0) | 6(10.2) | 5(50) |
| spl | 190(91.8) | 22(100) | 5(100) | 17(94.4) | 12(100) | 70(100) | 1(9.1)[b] | 54(91.5) | 9(90) |
| arcA | 0(0) | 0(0) | 0(0) | 0(0) | 0(0) | 0(0) | 0(0) | 0(0) | 0(0) |
| sea | 21(10.1) | 17(77.3) | 0(0) | 0(0) | 0(0) | 0(0) | 0(0) | 4(6.8) | 0(0) |
| seb | 0(0) | 0(0) | 0(0) | 0(0) | 0(0) | 0(0) | 0(0) | 0(0) | 0(0) |
| sec | 12(5.8) | 3(13.6) | 0(0) | 0(0) | 0(0) | 2(2.9) | 0(0) | 6(10.2) | 1(10) |
| sed | 24(11.6) | 0(0) | 0(0) | 2(11.1) | 8(66.7) | 6(8.6) | 0(0) | 6(10.2) | 2(20) |
| see | 16(7.7) | 0(0) | 0(0) | 1(5.6) | 0(0) | 0(0) | 1(9.1) | 9(15.3) | 5(50) |
| seg | 63(30.4) | 3(13.6) | 0(0) | 18(100)[b] | 12(100)[b] | 8(11.4) | 0(0) | 18(30.5) | 4(40) |
| seh | 24(11.6) | 22(100) | 0(0) | 0(0) | 0(0) | 0(0) | 0(0) | 2(3.4) | 0(0) |
| sei | 94(45.4) | 3(13.6) | 1(20) | 18(100)[b] | 12(100)[b] | 18(25.7) | 2(18.2) | 33(55.9) | 7(70) |
| selj | 25(12.1) | 3(13.6) | 0(0) | 0(0) | 0(0) | 11(15.7) | 2(18.2) | 8(13.6) | 1(10) |
| selk | 46(22.2) | 14(63.6) | 0(0) | 1(77.8) | 0(0) | 2(2.9)[b] | 5(45.5) | 9(15.3) | 2(20) |
| sell | 9(4.3) | 3(16.7) | 0(0) | 0(0) | 0(0) | 0(0) | 0(0) | 5(8.5) | 1(10) |
| selm | 58(28.0) | 2(9.1) | 0(0) | 18(100)[b] | 11(91.7)[b] | 5(7.1) | 0(0) | 18(30.5) | 4(40) |
| seln | 60(29.0) | 2(9.1) | 0(0) | 18(100)[b] | 12(100)[b] | 1(1.4) | 0(0) | 22(37.3) | 5(50) |
| selo | 65(31.4) | 0(0) | 2(40) | 18(100)[b] | 12(100)[b] | 3(4.3) | 1(9.1) | 23(39.0) | 6(60) |
| selp | 8(3.9) | 3(13.6) | 1(20) | 0(0) | 0(0) | 1(1.4) | 0(0) | 2(3.4) | 1(10) |

TABLE 2-continued

| Genes | Total(207) | CC1(n = 22) | CC8(n = 5) | CC20(n = 18) | CC72(n = 12) | CC188(n = 70) | CC398(n = 11) | Others( n = 259) | NT(n = 10) |
|---|---|---|---|---|---|---|---|---|---|
| selq | 90(43.5) | 16(72.7) | 1(20) | 9(50) | 0(0) | 34(48.6) | 1(9.1)[b] | 29(49.2) | 0(0) |
| selr | 8(3.9) | 0(0) | 0(0) | 0(0) | 0(0) | 5(7.1) | 0(0) | 2(3.4) | 1(10) |
| selu | 13(6.3) | 0(0) | 0(0) | 5(27.8) | 0(0) | 1(1.4) | 1(9.1) | 5(8.5) | 1(10) |
| tst-1 | 5(2.4) | 0(0) | 0(0) | 0(0) | 0(0) | 2(2.9) | 2(18.2) | 1(1.7) | 0(0) |
| SCCmec | 23(11.1) | 1(5.6) | 0(0) | 1(5.6) | 7(58.3)[b] | 8(11.4) | 0(0) | 6(10.1) | 0(0) |

[a]Number in parenthesis indicates a ratio of positive isolates in each group[b]. The difference is significant at the 05 by one-way ANOVA for multiple comparisons (P <05)

Example 2. Identification of Pathogenic Factor of Staphylococcus aureus

Staphylococcus aureus has various pathogenic factors such as cytotoxin, enterotoxin, cell adhesion factor, and antibiotic resistance gene. Pathogenic factors of 50 kinds of Staphylococcus aureus can be identified by multiplex PCR. The multiplex PCR method was used to identify pathogenicity genes of 207 strains isolated by type.

Example 3. Preparation of Attenuated Enterotoxin and Cytotoxin Protein

Example 3-1. Preparation of Attenuated Enterotoxin Protein

In order to prepare Korean mastitis vaccine, attenuated mutant clones were constructed for highly expressed Staphylococcus aureus enterotoxins SEG, SEI, SEM, SEN and SEO. Each enterotoxin amino acid substitution site was substituted by overlapping PCR method using a primer having a nucleotide sequence substituted with histidine and aspartic acid of enterotoxin involved in high binding with MHC class II of antigen-presenting cells. Each of the substituted protein sequences was transferred to a vector having his-tag to be purified by the imidazole concentration gradient method. The nucleotide sequence and amino acid sequence of the attenuated enterotoxin prepared by the method are shown in Table 3. In Table 3, the bolded part indicates the substitution site thereof.

TABLE 3

| SEQ ID NO. | name | Sequence |
|---|---|---|
| 1 | Mutant SEG | caacccgatcctaaattagacgaactaaataaagtaagtgattataaaaataataagggaactatgggtgctgta<br>atgaatctttatacgtctccacctgttgaaggaagaggagttattaattctagacagttttatctcatgatttaatttttc<br>caattgagtataagagttataatgaggttaaaactgaattagaaaatacagaattagctaacaattataaagataaa<br>aaagtagacattttggcgttccatatttttatacatgtataatacctaaatctgaaccggatataaaccaaattttgg<br>aggttgttgtatgtatggtggtcttacatttaatagttcagaaaatgaaagagataaattaattactgtacaggtaaca<br>atcgacaatagacaatcacttggatttacaataactacaaataagaatatggttactattcaggaactagattacaa<br>agcaagacactggctcactaaagaaaaaaagctatacgaggctgctggttctgcatttgaatctggatatataaa<br>atttactgaaaagaacaatacaagtttttggtttgacttatttcctaaaaaagaactagtaccttttgttccatataagtt<br>tttaaatatttacggagataataaagttgttgattctaagagtattaaaatggaagtatttcttaatactcactga |
| 2 | Mutant SEG | QPDPKLDELNKVSDYKNNKGTMGAVMNLYTSPPVEGRGVINSRQFLS<br>HDLIFPIEYKSYNEVKTELENTELANNYKDKKVDIFGVPYFYTCIIPKSE<br>PDINQNFGGCCMYGGLTFNSSENERDKLITVQVTIDNRQSLGFTITTNK<br>NMVTIQELDYKARHWLTKEKKLYEAAGSAFESGYIKFTEKNNTSFWF<br>DLFPKKELVPFVPYKFLNIYGDNKVVDSKSIKMEVFLNTH |
| 3 | Mutant SEI | Gatattggtgtaggtaacttaagaaatttctatacaaaacatgattatatagatttaaaaggcgtcacagataaaaa<br>cctacctattgcaaatcaactcgaattttcaacaggtaccaatgatttgatctcagaatctaataattgggacgaaat<br>aagtaaatttaaaggaaagaaactggatatttttggcattgattataatggtccttgtaaatctaaatacatgtatgga<br>ggggccactttatcaggacaatacttaaattctgctagaaaaatccctattaatctttgggttaatggcaaacataaa<br>acaatttctactgacaaaatagcaactaataaaaaactagtaacagctcaagaaattgatgttaaattaagaagata<br>tcttcaagaagaatacaatatatatggtaataataacactggtaaaggcaaagaatatggatataaatctaaatttta<br>ttcaggttttaataatgggaaagttttatttcatttaaataatgaaaaatcattttcatatgatttgttttatacaggagat<br>ggactgcctgtaagtttttgaaaatttatgaagataataaaataatagaatctgaaaaatttgctcttgctgtcgaaa<br>tatcatatgtagatagtaactaa |
| 4 | Mutant SEI | DIGVGNLRNFYTKHDYIDLKGVTDKNLPIANQLEFSTGTNDLISESNN<br>WDEISKFKGKKLDIFGIDYNGPCKSKYMYGGATLSGQYLNSARKIPIN<br>LWVNGKHKTISTDKIATNKKLVTAQEIDVKLRRYLQEEYNIYGNNNT<br>GKGKEYGYKSKFYSGFNNGKVLFHLNNEKSFSYDLFYTGDGLPVSFL<br>KIYEDNKIIESEKFALAVEISYVDSN |
| 5 | Mutant SEM | Gatgtcggagttttgactcttaggaactattatggtagctatccaattgaagaccaccaaagtattaatcctgaaaa<br>taatcatctttcgcatcaattagtttttctatggataattcgacagtaacagctgaatttaagaacgttgatgatgtaa<br>agaaattcaaaaatcatgctgtagatgtatatggtctaagttatagtggatattgtttgaaaaacaaatatatatacg<br>gtggagttacattagcaggtgattatttagagaaatctagacgtattcctattaatctttgggttaatggagaacatc<br>aaactatatctactgacaaagtatcaactaataaaaagttagtaacagctcaagaaattgatactaaattaagaaga<br>tatctacaagaagaatataatatttatggctttaatgatacaaataaaggaagaaattatggtaataagtcaaaattta<br>gttctggatttaatgcaggaaaaatattatttcatttgaatgatggttcatcattttcttatgacttatttgatactggaac<br>aggacaagctgaaagtttcttaaaaatatataatgacaacaaaactgtcgaaactgaaaaattcgctttagctgta<br>gaaatatcttataaggacgaaagttga |

TABLE 3-continued

| SEQ ID NO. | name | Sequence |
|---|---|---|
| 6 | Mutant SEM | DVGVLTLRNYYGSYPIEDHQSINPENNHLSHQLVFSMDNSTVTAEFKN<br>VDDVKKFKNHAVDVYGLSYSGYCLKNKYIYGGVTLAGDYLEKSRRIP<br>INLWVNGEHQTISTDKVSTNKKLVTAQEIDTKLRRYLQEEYNIYGFND<br>TNKGRNYGNKSKFSSGFNAGKILFHLNDGSSFSYDLFDTGTGQAESFL<br>KIYNDNKTVETEKFALAVEISYKDES |
| 7 | Mutant SEN | Gaagtagacaaaaaagatttaaagaaaaaatctgatctagatagtagtaagttatttaatttaacaagctattatact<br>gatataacgtggcaattagacgagtcaaataaaattagtacagatcaactactgaataatactataatattaaaaaa<br>tattgatatatccgtacttaaaacttctagtttgaaagttgagtttaactcatcagatttagcaaatcaatttaaaggaa<br>aaaatatagatatttatggactgtattttggaaataaatgtgtaggcttaactgaagaaaaaacatcatgcttatacg<br>gaggagttacgatacatgatggaaatcaattagatgaagagaaagttataggcgttaatgtatttaaagatggtgt<br>ccaacaagaaggttttgttataaaaaccaaaaaggctaaagtaacagtacaagaattagacactaaagttcgattt<br>aaattagaaaatttatataaaatatacaataaagataccggtaacatacaaaaaggatgcatttctttcattctcata<br>atcatcaagatcaatcattttattatgatttatataacgtaaaaggttcagtgggagcagagtttttcaattttatagtg<br>ataatagaacagttagctcatctaattatgctattgctgtatttttatataaagattaa |
| 8 | Mutant SEN | EVDKKDLKKKSDLDSSKLFNLTSYYTDITWQLDESNKISTDQLLNNTII<br>LKNIDISVLKTSSLKVEFNSSDLANQFKGKNIDIYGLYFGNKCVGLTEE<br>KTSCLYGGVTIHDGNQLDEEKVIGVNVFKDGVQQEGFVIKTKKAKVT<br>VQELDTKVRFKLENLYKIYNKDTGNIQKGCIFFHSHNHQDQSFYYDLY<br>NVKGSVGAEFFQFYSDNRTVSSSNYAIAVFLYKD |
| 9 | Mutant SEO | Aatgaagaagatcctaaaatagagagtttgtgtaagaagtcaagtgtagaccctattgctttacataatattaatga<br>tgattatataaataatcgatttacgacagtaaaatcaattgtatcaactacagaaaaattcttagacttcgatttattatt<br>taaaagtattaattggttagatggaatatctgctgaatttaaagatttaaaagtggaatttagctcatcagcgatttcta<br>aagaatttctaggaaagactgagatatttatggtgtttactataaagcacattgtcgtggtgagcatcaagtggata<br>ctgcctgtacatatggtggggtaacacctcatgaaaataataaattaagcgagcctaaaaatataggagtagctgt<br>gtataaggataatgtaaatgttaatacatttatcgttactacagataaaaagaaagttactgcacaagaacttgatat<br>taaagtaagaacaaaattaaataatgcatataaattgtatgacagaatgactagtgatgtacaaaaaggttatatta<br>aatttcattctcattcggagcataaagaatcattttattatgatttattttatattaaaggaaatttaccagatcaatatttg<br>caaatttataatgataataaaacaatagattcatcagactatgctattgctgatatttatttacataa |
| 10 | Mutant SEO | NEEDPKIESLCKKSSVDPIALHNINDDYINNRFTTVKSIVSTTEKFLDFD<br>LLFKSINWLDGISAEFKDLKVEFSSSAISKEFLGKTVDIYGVYYKAHCR<br>GEHQVDTACTYGGVTPHENNKLSEPKNIGVAVYKDNVNVNTFIVTTD<br>KKKVTAQELDIKVRTKLNNAYKLYDRMTSDVQKGYIKFHSHSEHKES<br>FYYDLFYIKGNLPDQYLQIYNDNKTIDSSDYAIAVYLFT |

Example 3-2. Preparation of Cytotoxin Protein

In order to easily purify each cytotoxin of the isolated *Staphylococcus aureus*, it was constructed such that Staphylococcal exfoliative toxin A promoter (ETA promoter) and a signal peptide sequence of *Staphylococcus aureus* strain LAC strain was linked to cytotoxin coding sequence and when the cytotoxin prepared in the cell was transferred toward the cell wall, AXA motif was cleaved by the endopeptidase so that only pure cytotoxin was secreted out of the cell. The prepared gene was cloned into Pmk4 vector and transformed into *S. aureus* RN4220, a protein expression host so that the desired cytotoxin was contained in the bacterial culture medium. The cytotoxin of the bacterial culture was finally purified through a hydrophobic column. The sequences used in the method and nucleotide sequences and amino acid sequences of cytotoxin of the present invention prepared therefrom are shown in Table 4. The sequence represented by the bold in the nucleotide sequences shown in Table 4 indicates a signal peptide.

TABLE 4

| SEQ ID. NO | NAME | Sequence |
|---|---|---|
| 11 | ETA promoter | Aaatatcaacgtgagggctctagtactaacgatttttttgtgcagtatgtagaatcactgacaaggaacaaa<br>agattaaaaatgaaaaatattggggaactattgagtggaattaacaaacgtatttaatgatagttaattaaaag<br>ttaataaaaaataatttgttttgaaatagaaacgttatataatttttaatgtattcgaatacattaaaaaacgcaaat<br>gttaggatgattaata |
| 12 | H1gA signal peptide | Atgattaaaaataaaatattaacagcaactttagcagttggtttaatagcccctttagccaatccatttatagaa<br>atttctaaagca |
| 13 | H1gA mature protein | Gaaaataagatagaagatatcggccaaggtgcagaaatcatcaaaagaacacaagacattactagcaaa<br>cgattagctataactcaaaacattcaatttgattttgtaaaagataaaaaatataacaaagatgccctagttgtt<br>aagatgcaaggcttcattagctctagaacaacatattcagacttaaaaaaatatccatatattaaaagaatgat<br>atggccatttcaatataatatcagtttgaaaacgaaagactctaatgttgatttaattaattatcttcctaaaaata<br>aaattgattcagcagatgttagtcagaaattaggctataatatcggcggaaacttccaatcagcgccatcaat<br>cggaggcagtggctcattcaactactctaaaacaattagttataatcaaaaaaactatgttactgaagtagaa |

TABLE 4-continued

| SEQ ID. NO | NAME | Sequence |
|---|---|---|
| | | agtcagaactctaaaggtgttaaatggggagtgaaagcaaattcattcgttacaccgaatggtcaagtatct<br>gcatatgatcaatacttatttgcacaagacccaactggtccagcagcacgagactatttcgtcccagataatc<br>aactacctcctttaattcaaagtggctttaatccatcatttattacaacattgtcacacgaaagaggtaaaggtg<br>ataaaagcgagtttgaaatcacttacggcagaaacatggatgctacatatgcttacgtgacaagacatcgttt<br>agccgttgatagaaaacatgatgcttttaaaaaccgaaacgttacagttaaatatgaagtgaactggaaaac<br>acatgaagtaaaaattaaaagcatcacacctaagtaa |
| 14 | ETA-H1gA | aaatatcaacgtgagggctctagtactaacgatttttttgtgcagtatgtagaatcactgacaaggaacaaaa<br>gattaaaaatgaaaaatattggggaactattgagtggaattaacaaacgtatttaatgtttagttaattaaaagtt<br>aataaaaaataatttgttttgaaatagaaacgttatataatttttaatgtattcgaatacattaaaaaacgcaaatg<br>ttaggatgattaataatgattaaaaataaaatattaacagcaactttagcagttggtttaatagccccttt<br>agccaatccatttatagaaatttctaaagcagaaaataagatagaagatatcggccaaggtgcagaaat<br>catcaaaagaacacaagacattactagcaaacgattagctataactcaaaacattcaatttgattttgtaaaag<br>ataaaaaatataacaaagatgccctagttgttaagatgcaaggcttcattagctctagaacaacatattcaga<br>cttaaaaaaatatccatatattaaaagaatgatatggccatttcaatataatatcagtttgaaaacgaaagactc<br>taatgttgatttaattaattatcttcctaaaaataaaattgattcagcagatgttagtcagaaattaggctataatat<br>cggcggaaacttccaatcagcgccatcaatcggaggcagtggctcattcaactactctaaaacaattagtta<br>taatcaaaaaaactatgttactgaagtagaaagtcagaactctaaaggtgttaaatggggagtgaaagcaaa<br>ttcattcgttacaccgaatggtcaagtatctgcatatgatcaatacttatttgcacaagacccaactggtccag<br>cagcacgagactatttcgtcccagataatcaactacctcctttaattcaaagtggctttaatccatcatttattac<br>aacattgtcacacgaaagaggtaaaggtgataaaagcgagtttgaaatcacttacggcagaaacatggatg<br>ctacatatgcttacgtgacaagacatcgtttagccgttgatagaaaacatgatgcttttaaaaaccgaaacgtt<br>acagttaaatatgaagtgaactggaaaacacatgaagtaaaaattaaaagcatcacacctaagtaa |
| 15 | H1gA | ENKIEDIGQGAEIIKRTQDITSKRLAITQNIQFDFVKDKKYNKDALV<br>VKMQGFISSRTTYSDLKKYPYIKRMIWPFQYNISLKTKDSNVDLIN<br>YLPKNKIDSADVSQKLGYNIGGNFQSAPSIGGSGSFNYSKTISYNQK<br>NYVTEVESQNSKGVKWGVKANSFVTPNGQVSAYDQYLFAQDPTG<br>PAARDYFVPDNQLPPLIQSGFNPSFITTLSHERGKGDKSEFEITYGRN<br>MDATYAYVTRHRLAVDRKHDAFKNRNVTVKYEVNWKTHEVKIK<br>SITPK |
| 16 | H1gC signal peptide | Atgcttaaaaataaaatattaactacaactttatctgtgagcttacttgcccctcttgccaatccgttattagaaa<br>atgctaaagct |
| 17 | H1gC mature protein | gctaacgatactgaagacatcggtaaaggaagcgatatagaaattatcaaaggacagaagataaaacaa<br>gtaataaatggggcgtgactcaaaatattcaatttgattttgtaaaggataaaaaatataacaaagatgctttg<br>atattaaagatgcaaggattcattagctctagaacaacatattacaactataaaaaaactaatcatgttaaagc<br>tatgcgatggccattccaatataatattggtttaaaaacaaatgataaatatgtttctttaattaattatttacctaa<br>aaataaaattgaatctacaaacgtgagtcagacattaggatacaatatcggtggtaatttccaatcagcccca<br>tcactcggtggtaatggatcatttaactattctaaatcgattagctatacacaacaaaattatgtaagtgaagta<br>gaacaacaaaactcaaaaagtgttttatggggcgtcaaagcgaattcattcgccactgaatcaggtcaaaa<br>atcagcctttgatagcgatttatttgtaggctacaaacctcatagtaaagatcctagagattatttcgttccaga<br>cagtgagttaccacctcttgtacaaagtggatttaacccttcatttatcgccacagtatctcatgaaaaaggttc<br>aagcgatacaagcgaatttgaaattacttacggaagaaacatggatgtcactcatgccattaaaagatcaac<br>gcattatggcaacagttatttagacggacatagagtccataatgcatttgtaaatagaaactatactgtgaaat<br>acgaggtcaattggaagactcatgaaatcaaggtgaaaggacagaattga |
| 18 | ETA-H1gC | aaatatcaacgtgagggctctagtactaacgatttttttgtgcagtatgtagaatcactgacaaggaacaaaa<br>gattaaaaatgaaaaatattggggaactattgagtggaattaacaaacgtatttaatgtttagttaattaaaagtt<br>aataaaaaataatttgttttgaaatagaaacgttatataatttttaatgtattcgaatacattaaaaaacgcaaatg<br>ttaggatgattaataatgcttaaaaataaaatattaactacaactttatctgtgagcttacttgcccctctt<br>gccaatccgttattagaaaatgctaaagctgctaacgatactgaagacatcggtaaaggaagcgatata<br>gaaattatcaaaggacagaagataaaacaagtaataaatggggcgtgactcaaaatattcaatttgattttg<br>taaaggataaaaaatataacaaagatgctttgatattaaagatgcaaggattcattagctctagaacaacatat<br>tacaactataaaaaaactaatcatgttaaagctatgcgatggccattccaatataatattggtttaaaaacaaat<br>gataaatatgtttctttaattaattatttacctaaaaataaaattgaatctacaaacgtgagtcagacattaggata<br>caatatcggtggtaatttccaatcagccccatcactcggtggtaatggatcatttaactattctaaatcgattag<br>ctatacacaacaaaattatgtaagtgaagtagaacaacaaaactcaaaaagtgttttatggggcgtcaaagc<br>gaattcattcgccactgaatcaggtcaaaaatcagcctttgatagcgatttatttgtaggctacaaacctcata<br>gtaaagatcctagagattatttcgttccagacagtgagttaccacctcttgtacaaagtggatttaacccttcat<br>ttatcgccacagtatctcatgaaaaaggttcaagcgatacaagcgaatttgaaattacttacggaagaaacat<br>ggatgtcactcatgccattaaaagatcaacgcattatggcaacagttatttagacggacatagagtccataat<br>gcatttgtaaatagaaactatactgtgaaatacgaggtcaattggaagactcatgaaatcaaggtgaaagga<br>cagaattga |
| 19 | H1gC | ANDTEDIGKGSDIEIIKRTEDKTSNKWGVTQNIQFDFVKDKKYNKD<br>ALILKMQGFISSRTTYYNYKKTNHVKAMRWPFQYNIGLKTNDKYV<br>SLINYLPKNKIESTNVSQTLGYNIGGNFQSAPSLGGNGSFNYSKSISY<br>TQQNYVSEVEQQNSKSVLWGVKANSFATESGQKSAFDSDLFVGY<br>KPHSKDPRDYFVPDSELPPLVQSGFNPSFIATVSHEKGSSDTSEFEIT<br>YGRNMDVTHAIKRSTHYGNSYLDGHRVHNAFVNRNYTVKYEVN<br>WKTHEIKVKGQN |

TABLE 4-continued

| SEQ ID. NO | NAME | Sequence |
|---|---|---|
| 20 | LukE signal peptide | Atgtttaagaaaaaaatgttagctgcaactttgtcagtaggactgattgcacctttagcatctccgattcaaga atctagagca |
| 21 | LukE mature protein | Aatactaatattgaaaatattggtgatggtgctgaagtaatcaaacgtacggaggatgtaagtagtaagaaa tggggcgttactcaaaatgtccaattcgactttgtaaaagataaaaaatataacaaagacgctttaattgttaa aatgcaaggttttattaattccagaacttcattttcagatgtgaagggtagtggatatgaattaactaaacgaat gatttggccattccaatataatataggactgacgactaaagatccaaatgttagcttaatcaattaccttcctaa aaacaaaatagaaactactgatgttggtcaaacattaggatataacattggaggtaatttccagtcagcacca tctataggtggcaatggctcatttaattattctaaaacaattagttataccaaaagagttatgtcagtgaagta gacaagcaaaactcaaaatctgttaaatggggtgttaaagcaaacgaatttgttacgcctgatggaaaaaaa tctgcgcatgatagatatttattcgtacaaagtccaaatggtccaacaggttcagcaagagaatattttgctcc tgataatcaattgccaccttttagttcaaagtggctttaatccatcgtttatcactacactatcacatgaaaaaggt tcaagtgatacgagtgaatttgaaatttcatatggtagaaacttagatattacatatgcgactttattccctagaa ctggtatttacgcagaaagaaagcataatgcatttgtaaatagaaactttgtagttagatatgaagttaattgga aaacacacgaaattaaagtgaaaggacataattaa |
| 22 | ETA-LukE | aaatatcaacgtgagggctctagtactaacgatttttttttgtgcagtatgtagaatcactgacaaggaacaaaa gattaaaaatgaaaaatattggggaactattgagtggaattaacaaacgtatttaatgtttagttaattaaaagtt aataaaaaataatttgttttgaaatagaaacgttatataattttttaatgtattcgaatacattaaaaaacgcaaatg ttaggatgattaatatgtttaagaaaaaaatgttagctgcaactttgtcagtaggactgattgcacctttagcatctccgattcaagaatctagagcaaatactaatattgaaaatattggtgatggtgctgaagtaatcaaacgtacggaggatgtaagtagtaagaaatggggcgttactcaaaatgtccaattcgactttgtaaaagataaaaaatataacaaagacgctttaattgttaaaatgcaaggttttattaattccagaacttcattttcagatgtgaagggtagtggatatgaattaactaaacgaatgatttggccattccaatataatataggactgacgactaaagatccaaatgttagcttaatcaattaccttcctaaaaacaaaatagaaactactgatgttggtcaaacattaggatataacattggaggtaatttccagtcagcaccatctataggtggcaatggctcatttaattattctaaaacaattagttataccaaaagagttatgtcagtgaagtagacaagcaaaactcaaaatctgttaaatggggtgttaaagcaaacgaatttgttacgcctgatggaaaaaaatctgcgcatgatagatatttattcgtacaaagtccaaatggtccaacaggttcagcaagagaatattttgctcctgataatcaattgccaccttttagttcaaagtggctttaatccatcgtttatcactacactatcacatgaaaaaggttcaagtgatacgagtgaatttgaaatttcatatggtagaaacttagatattacatatgcgactttattccctagaactggtatttacgcagaaagaaagcataatgcatttgtaaatagaaactttgtagttagatatgaagttaattggaaaacacacgaaattaaagtgaaaggacataattaa |
| 23 | LukE | NTNIENIGDGAEVIKRTEDVSSKKWGVTQNVQFDFVKDKKYNKDA LIVKMQGFINSRTSFSDVKGSGYELTKRMIWPFQYNIGLTTKDPNV SLINYLPKNKIETTDVGQTLGYNIGGNFQSAPSIGGNGSFNYSKTISY TQKSYVSEVDKQNSKSVKWGVKANEFVTPDGKKSAHDRYLFVQS PNGPTGSAREYFAPDNQLPPLVQSGFNPSFITTLSHEKGSSDTSEFEI SYGRNLDITYATLFPRTGIYAERKHNAFVNRNFVVRYEVNWKTHEI KVKGHN |
| 24 | LukS signal peptide | atgaataatagtaaaattatttctaaagttttattgtgtcttatctctatttactgtaggagctagtgcatttgttattca agacgaactgatgcaaaaaaaccatgcaaaagca |
| 25 | LukS mature protein | Gataacaatattgagaatattggtgatggcgctgaggtagtcaaaagaacagaagatacaagtagcgata agtgggggtcacacaaaatattcagtttgattttgttaaagataaaaagtataacaaagacgctttgattttaa aaatgcaaggttttatcaattcaaagactacttattacaattacaaaaacacagatcatataaaagcaatgagg tggccttccaatacaatattggtctcaaaacaaatgacccccaatgtagatttaataaatttatcctacctaaaaat aaaatagattcagtaaatgttagtcaaacattaggttataacataggtggtaattttaatagtggtccatcaaca ggaggtaatggttcatttaattattcaaaaacaattagttataatcaacaaaactatatcagtgaagtagaacgt caaaaattcaaaaagtgttcaatggggaataaaagctaattcatttatcacatcattaggtaaaatgtctggaca tgatccaaattttatttgttggatataaaccatatagtcaaatccgagagactattttgttccagacaatgaatta cccccattagtacacagtggtttcaatccttcatttattgcaactgtttctcatgaaaaaggctcaggagataca agtgaatttgaaataacgtatggcagaaatggatgttactcatgctactagaagaacaacacactatggc aatagttatttagaaggatctagaatacaacgcatttgtaaacagaaattacacagttaaatatgaagtgaa ctggaaaactcatgaaattaaagtgaaaggacataattga |
| 26 | ETA-LukS | aaatatcaacgtgagggctctagtactaacgatttttttttgtgcagtatgtagaatcactgacaaggaacaaaa gattaaaaatgaaaaatattggggaactattgagtggaattaacaaacgtatttaatgtttagttaattaaaagtt aataaaaaataatttgttttgaaatagaaacgttatataattttttaatgtattcgaatacattaaaaaacgcaaatg ttaggatgattaatatgaataatagtaaaattatttctaaagttttattgtgtcttatctctatttactgtaggagctagtgcatttgttattcaagacgaactgatgcaaaaaaaccatgcaaaagcagataacaatattgagaatattggtgatggcgctgaggtagtcaaaagaacagaagatacaagtagcgataagtgggggtcacacaaaatattcagtttgattttgttaaagataaaaagtataacaaagacgctttgattttaaaaatgcaaggttttatcaattcaaagactacttattacaattacaaaaacacagatcatataaaagcaatgaggtggccttccaatacaatattggtctcaaaacaaatgacccccaatgtagatttaataaatttatcctacctaaaaataaaatagattcagtaaatgttagtcaaacattaggttataacataggtggtaattttaatagtggtccatcaacaggaggtaatggttcatttaattattcaaaaacaattagttataatcaacaaaactatatcagtgaagtagaacgtcaaaaattcaaaaagtgttcaatggggaataaaagctaattcatttatcacatcattaggtaaaatgtctggacatgatccaaattttatttgttggatataaaccatatagtcaaatccgagagactattttgttccagacaatgaattaccccccattagtacacagtggtttcaatccttcatttattgcaactgtttctcatgaaaaaggctcaggagatacaagtgaatttgaaataacgtatggcagaaatggatgttactcatgctactagaagaacaacacactatggcaatagttatttagaaggatctagaatacaacgcatttgtaaacagaaattacacagttaaatatgaagtgaactggaaaactcatgaaattaaagtgaaaggacataattga |

TABLE 4-continued

| SEQ ID. NO | NAME | Sequence |
|---|---|---|
| 27 | LukS | DNNIENIGDGAEVVKRTEDTSSDKWGVTQNIQFDFVKDKKYNKDA LILKMQGFINSKTTYYNYKNTDHIKAMRWPFQYNIGLKTNDPNVD LINYLPKNKIDSVNVSQTLGYNIGGNFNSGPSTGGNGSFNYSKTISY NQQNYISEVERQNSKSVQWGIKANSFITSLGKMSGHDPNLFVGYKP YSQNPRDYFVPDNELPPLVHSGFNPSFIATVSHEKGSGDTSEFEITY GRNMDVTHATRRTTHYGNSYLEGSRIHNAFVNRNYTVKYEVNWK THEIKVKGHN |

FIG. 1 illustrates the results of chromatographic analysis of recombinant proteins of attenuated enterotoxin and cytotoxin prepared and purified as described above.

Example 4. Mouse Challenge Test

In order to confirm the efficacy of the 5 kinds of attenuated enterotoxins (SAg) and 4 kinds of cytotoxins prepared in Example 3 as an antigen, a mouse challenge test was carried out as follows. Specifically, eight 3-week-old mice were set as one group. The total 4 groups were set: i.e., PBS-inoculated control group, enterotoxin-inoculated group (5 kinds: SEG, SEI, SEM, SEN and SEO), cytotoxin-inoculated group (4 kinds: HlgA, HlgC, LukE and LukS) and mixture with enterotoxin and cytotoxin-inoculated group (SEG, SEI, SEM, SEN, SEO, HlgA, HlgC, LukE and LukS). Each of the antigens was inoculated twice in 10 μg each for 14 days. On the 28th day after the first inoculation, *S. aureus* K30 at a concentration of $2\times10^9$ CFU was intraperitoneally subject to challenge test. Therefore, the survival rate was confirmed for 7 days so as to confirm the efficacy of an antigen. The results are illustrated in FIG. 2.

As illustrated in FIG. 2, the survival rate of the control group was 0%, while the survival rate was increased in the enterotoxin-inoculated group and the cytotoxin-inoculated group. In particular, the group inoculated with enterotoxin and cytotoxin showed 100% of survival rate, indicating that the vaccine prepared by mixing enterotoxin and cytotoxin of the present invention shows excellent effect.

Example 5. Determination of Optimal Amount of Antigen

In order to determine the amount of antigen that induces an optimal antibody response, 5, 10, 25, 50, 100, and 150 μg of attenuated enterotoxin and cytotoxin gene recombinant proteins, respectively were first diluted with PBS to be a final volume of 2 ml. Then, 8 ml of aluminum hydroxide gel (2%) was added thereto, and they were mixed well. The mixture was subcutaneously inoculated into mesogluteus of 3 dairy cattles with dry milk period, respectively, at 2-week intervals, 2 times each. Further, at 2 weeks after the last inoculation, the serum was separated and the antibody titers to the specific antigens were measured using the total IgG antibody and the sandwich ELISA in the serum. The results are illustrated in FIG. 3.

As illustrated in FIG. 3, the IgG antibody titers according to the amount of antigen were measured. The results indicated that the antibody did not change in the antigen of 50 μg or more. Therefore, the final concentration of the vaccine inoculation was determined as 100 μg for each antigen considering individual differences.

Example 6. Confirmation of Safety of Vaccine

In order to examine the stability of enterotoxin and cytotoxin vaccine of the present invention, vaccine containing 50 μg (2 counts), 150 μg (6 counts) and 300 μg (8 counts) of the enterotoxin (5 kinds) and cytotoxin (4 kinds), respectively, were inoculated to pregnant dairy cattle (Holstein) two times every two weeks. The safety of the vaccine was evaluated until delivery. In order to evaluate the safety, the somatic cell count and the amount of milk production were compared in the vaccine-inoculated group and the control group. The results are illustrated in FIG. 4. In FIG. 4, the red graph represents the vaccine-inoculated group, and the blue graph represents the control group.

As illustrated in FIG. 4, the results indicated that all of the dairy cattles used in the experiment gave birth to normal calves on the scheduled date, and no abnormality was found in the calves and cows. Further, there were no found side effects such as intramammary infections, changes in somatic cells of raw milk, and changes in milk production, confirming the safety of vaccine comprising enterotoxin and cytotoxin of the present invention.

Example 7. Confirmation of Vaccine's Preventive or Therapeutic Effect on Mastitis In order to demonstrate the preventive effect on mastitis of the vaccine of the present invention, the effect of the challenge test on dairy cattle was examined as follows. Specifically, a total of 4 Holstein cows with no infectivity of *Staphylococcus aureus* were inoculated with the control group (PBS+aluminum hydroxide gel) and the vaccine groups (a total of 500 μg (each 100 μg) of attenuated enterotoxin (5 kinds of enterotoxins)+a total of 400 μg (each 100 μg) of attenuated cytotoxin (4 kinds of cytotoxins)+aluminum hydroxide gel) at 2 times in dry milk period and 1 time in milk period. Then, *Staphylococcus aureus* (K30) was diluted in PBS. The challenge test was performed with the nipple of the control group (4 to 10 CFU inoculation) and the experimental group (43 to 48 CFU and 83 to 95 CFU inoculation), confirming the effects. The results of the control group are illustrated in FIG. 5. The results of inoculation of 43 to 48 CFU *Staphylococcus aureus* in the vaccine group are illustrated in FIG. 6A (45 and 48 CFU) and FIG. 6B (43 and 46 CFU). The results of inoculation of 83 to 95 CFU *Staphylococcus aureus* in the vaccine group are illustrated in FIG. 7A (88 and 95 CFU) and FIG. 7B (83 and 89 CFU).

As illustrated in FIG. 5, the control group showed increase of the bacterial count, increase of the somatic cell count, increase of the body temperature and decrease of the milk production in the dairy cattle after 1 to 3 days in the 4 to 10 CFU *Staphylococcus aureus* (K30) challenge test. Necrotizing mastitis accompanied by fever was observed.

On the other hand, as illustrated in FIGS. 6A and 6B, the vaccine group showed that no bacterial infection was detected in 43 to 48 CFU Staphylococcus aureus (K30) inoculation on four dairy cattles, and clinical signs of mastitis such as the increase of the somatic cell count, increase of the body temperature and decrease of the milk production were not identified.

Further, as illustrated in FIGS. 7A and 7B, the vaccine group showed that temporary mastitis symptoms were detected in 83 to 95 CFU Staphylococcus aureus (K30) inoculation on four dairy cattles, but it was found that all of them were cured naturally after 7 days to 9 days.

These results confirm that the vaccine according to the present invention exhibits an effective prevention and treatment effect on bovine mastitis even in a high CFU Staphylococcus aureus challenge test compared with the control group.

Example 8. Confirmation of Cross-Reaction of Cytotoxin Vaccine Antibody

For the economics of industrialization of vaccines, there is a need to develop a vaccine that can be effective although the number of antigens required for the vaccine is decreased. Accordingly, in this Example, the cross-reaction of four kinds of cytotoxins (HlgA, HlgC, LukE, LukS) used in the present invention was confirmed. For this Example, first, cytotoxin antigens were individually mixed with a vaccine adjuvant (Freund's adjuvant). The mixture was subcutaneously injected into C57BL/C mice three times at 2-week intervals to obtain serum according to the single antigen. Further, before measuring the cross-neutralizing antibody response to cytotoxin, susceptibility test for cytotoxin of Bovine Leukocyte used as a control group was performed. Then, 4 kinds of currently used S-component antigens (HlgA, HlgC, LukE and LukS) and 3 kinds of the remaining F-component antigens (HlgB, LukD and LukF) were combined for the neutralizing ability test of 7 kinds of cytotoxins (HgA, HlgB, HlgC, LukD, LukE, LukF and LukS). They were reacted with Leukocyte obtained from dairy cattles. Therefore, the intracellular penetration of propidium iodide, an indicator of cell membrane damage, was measured by flow cytometry. The results are illustrated in FIG. 8. As illustrated in FIG. 8, the cytotoxin combination showing strong cytotoxicity to bovine leukocyte was HlgB/HlgA, LukD/HlgA, HlgB/HlgC, LukD/HlgC, HlgB/LukE, LukD/LukE, HlgB/LukS or LukD/LukS. Further, Bovine Leukocyte showed the most sensitive response to cytotoxin of HlgA/HlgB, HlgA/LukD, LukE/HlgB and LukE/LukD combination, but it showed the weakest response to LukF cytotoxin among the combinations.

The mean fluorescence intensity (MFI) is a geometric mean scale with a 10-time difference in MFI 10 and a 500-time fluorescence difference in MFI 20, indicating a significant difference in MFI 25 and above. It was confirmed that the MFI of the control group without administering cytotoxin was 5.2.

Accordingly, the combination of cytotoxin with the minimum concentration of cytotoxin that induces a mean fluorescence intensity (MFI) of 25 or more among the confirmed cytotoxin combinations and immune serum (1000 times dilution) to each of cytotoxin vaccine candidates of 4 kinds of cytotoxins of the present invention, which were prepared from mice, were mixed at a ratio of 1:1, and the neutralizing ability was measured. The results are illustrated in FIG. 9.

As illustrated in FIG. 9, it was confirmed that immune serum (aHlgA and aLukE) for HlgA and LukE showed a neutralizing antibody response that cross-protected to 35% or less of the cytotoxicity for cytotoxin combination such as HlgA/HlgB, HlgA/LukD, LukE/HlgB, LukE/LukD and HlgC/LukD as the results of measuring neutralizing ability of cytotoxin using neutralizing antibodies. Further, it was confirmed that immune serum (aLukS) for LukS showed a neutralizing antibody response that cross-protected to 35% or less of the cytotoxicity for cytotoxin combination such as LukE/HlgB, LukE/LukD, LukS/HlgB and LukS/LukD.

This result shows that all combinations of cytotoxin can be neutralized by using only HlgA, LukE and LukS without including all 4 kinds of cytotoxins (HlgA, HlgC, LukE and LukS) in the present invention.

Example 9. Confirmation of Cross-Reaction of Enterotoxin Vaccine Antibody

In this Example, the cross-reaction of five enterotoxin (SEG, SEI, SEM, SEN, SEO) vaccines used in the present invention was confirmed. For this Example, first, enterotoxin antigens were individually mixed with a vaccine adjuvant (Freund's adjuvant). The mixture was subcutaneously injected into dairy cattle, a target animal, two times at 2-week intervals to obtain serum according to the single antigen. Then, in order to measure the cross-neutralizing antibody response to enterotoxin, T cells isolated from dairy cattle blood were treated with 5 kinds of enterotoxin vaccines, respectively. Then, each enterotoxin antigen was treated to confirm T cell differentiation ability. The results are illustrated in FIG. 10.

As illustrated in FIG. 10, it was confirmed that SEM antibody (a-SEM) neutralized SEN and SEO toxin antigens, and thus they did not act as an antigen, resulting in significantly decreased T cell differentiation ability as a result of cross-reacting with neutralizing antibody against enterotoxin (*; $p<0.01$,**; $p<0.05$). Therefore, it was confirmed that enterotoxin of the present invention can neutralize all kinds of enterotoxin antigens even if there are only 3 kinds of SEG, SEI and SEM rather than all 5 kinds of enterotoxins.

Example 10. Confirmation of Preventive or Therapeutic Effect on Mastitis of Vaccine Comprising Cytotoxin and Enterotoxin Having Neutralizing Ability In order to confirm the mastitis-preventive effect of the vaccine including the three kinds of cytotoxins (HlgA, LukE and LukS) and three kinds of enterotoxins (SEG, SEI and SEM) of the present invention having the neutralizing ability as confirmed in Examples 8 and 9, the effect of challenge test on dairy cattles was confirmed as follows. In particular, the 6 kinds of toxins (SEG, SEI, SEM, HlgA, LukE, and LukS), which were confirmed to have the neutralizing ability, were used as an antigen. 200 μg of each toxin was mixed with the same amount of aluminum hydroxide gel to prepare a vaccine. The vaccine was inoculated to a dairy cattle two times at intervals of two weeks. Then, *Staphylococcus aureus* (K30) 26CFU was challenge-tested to measure changes in bacterial count, somatic cell count, body temperature and milk production. The results are illustrated in FIG. 11.

As illustrated in FIG. 11, the vaccine group of the present invention showed no intramammary infection in the dairy cattle on 26 CFU *Staphylococcus aureus* (K30) inoculation, and mastitis clinical symptoms such as increase of the somatic cell count, the increase of the body temperature and the decrease of milk production were not detected.

Therefore, it was confirmed that vaccine including 6 kinds of toxins (SEG, SEI, SEM, HlgA, LukE and LukS) having neutralizing ability without including all 9 kinds of cytotoxin and enterotoxin of the present invention showed effective prevention and treatment of bovine mastitis.

Comparative Example 1. Experiment of Efficacy of Conventional Vaccine

Currently, there are 2 kinds of imported bovine mastitis vaccines (Lavac Staph® and STARTVAC® from Hipra) and 5 kinds of domestic vaccines in Korea. Among them, Lavac Staph® and STARTVAC® from Hipra have been sold for the last three years (2015 to 2017). Accordingly, in order to compare the efficacy of the vaccines of the present invention with the two commercially available products, one dairy cattle was inoculated three times according to the usage dose of Lavac Staph® and STARTVAC® from Hipra, followed by the challenge test. The results of experiments on Lavac Staph® and STARTVAC® from Hipra are shown in Table 5 and Table 6, respectively.

TABLE 5

| Test list | challenge test | | challenge test + $1^{st}$ day | | challenge test + $2^{nd}$ day | |
|---|---|---|---|---|---|---|
| | morning | afternoon | morning | afternoon | morning | afternoon |
| Somatic cell count (*1000) | 9 | 73 | 4 | — | — | — |
| Bacterial count in milk (cfu/ml) | 0 | 0 | 0 | — | — | — |
| Temperature (° C.) | 38.5 | 38.4 | 40.8 | 41.8 | 42.6 | |
| Total amount of milk (Kg) | 14 | 10 | 12 | 8 | 0 | 0 |
| Clinical symptom | No symptom | No symptom | Fasting | Fasting | Fasting | Killed |

As shown in Table 5, in the case of the Lavac Staph vaccine, the body temperature was raised to 40° C. after one day of *Staphylococcus aureus* 23 CFU challenge test, and symptoms such as no eating feed were shown. Then, it was confirmed that the dairy cattle was killed in the afternoon on the 2nd day after the challenge test. Further, it was confirmed that the challenge test strain was isolated from the mammary tissue sample of the killed dairy cattle.

TABLE 6

| Test list | challenge test | | challenge test +1st day | | challengege test + $2^{nd}$ day | | challenge test + $3^{rd}$ day | | challenge test + $4^{th}$ day | |
|---|---|---|---|---|---|---|---|---|---|---|
| | morning | afternoon | morning | afternoon | morning | afternoon | morning | afternoon | morning | afternoon |
| Somatic cell count (*1000) | 19 | 109 | 87 | 375 | 1,500 | — | — | — | — | — |
| Bacterial count in Milk (cfu/ml) | 0 | 0 | 3,200 | 70,000 | 345,000 | — | — | — | — | — |
| Temperature (° C.) | 38.5 | 38.4 | 38.4 | 40.1 | 42.3 | 42.2 | 42.3 | — | — | — |
| Total amount of milk (Kg) | 14 | 5.4 | 14.4 | 4.2 | 2 | 0 | 0 | 0 | 0 | 0 |
| Clinical symptom | No symptom | No symptom | No symptom | Temperature increase | Fasting | Fasting | Fasting | Fasting | Fasting | Killed |

As shown in Table 6, in the case of the STARTVAC® from Hipra vaccine, the body temperature was raised to 40° C. after one day of *Staphylococcus aureus* 21 CFU challenge test, and symptoms such as no eating feed were shown. Further, it was confirmed that the challenge test strain was isolated from the milk. Then, it was confirmed that the dairy cattle was killed in the afternoon on the 4th day after the challenge test. Therefore, it was confirmed that dairy cattles were killed within 4 days even in a low amount of 21 to 23 CFU of *Staphylococcus aureus* as the results of inoculating Lavac Staph and STARTVAC® from Hipra mastitis vaccines on dairy cattles, followed by the challenge test. On the other hand, the vaccine of the present invention showed no clinical symptoms of mastitis such as increased somatic cell count, increased body temperature and reduced milk production in 4 dairy cattles, which were the subjects of the experiment, even when 43 to 48 CFU of *Staphylococcus aureus* (K30) inoculation. It was confirmed that temporary mastitis symptoms were also observed at inoculation with 83 to 95 CFU of *Staphylococcus aureus* (K30), but after 7 to 9 days, all of them were naturally cured.

What is claimed is:

1. A *Staphylococcus aureus* enterotoxin protein comprising the amino acid sequence selected from the group consisting of SEQ ID NO: 2, SEQ ID NO: 4, SEQ ID NO: 6, SEQ ID NO: 8 and SEQ ID NO: 10.

2. The *Staphylococcus aureus* enterotoxin protein according to claim 1, wherein the amino acid sequence represented by SEQ ID NO: 2 is encoded by SEQ ID NO: 1,
the amino acid sequence represented by SEQ ID NO: 4 is encoded by SEQ ID NO: 3,
the amino acid sequence represented by SEQ ID NO: 6 is encoded by SEQ ID NO: 5,
the amino acid sequence represented by SEQ ID NO: 8 is encoded by SEQ ID NO: 7, and
the amino acid sequence represented by SEQ ID NO: 10 is encoded by SEQ ID NO: 9.

3. A vaccine composition for treating or preventing bovine mastitis, the vaccine composition comprising three *Staphylococcus aureus* enterotoxin proteins represented by SEQ ID NO: 2, SEQ ID NO: 4 and SEQ ID NO: 6 and three *Staphylococcus aureus* cytotoxin proteins amino acid represented by SEQ ID NO: 15, SEQ ID NO: 23 and SEQ ID NO: 27.

4. The vaccine composition according to claim 3, wherein the *Staphylococcus aureus* enterotoxin proteins and the *Staphylococcus aureus* cytotoxin proteins present in the vaccine composition in a ratio of 1:0.5 to 1:1.5 (w/w).

5. The vaccine composition according to claim 3, wherein each of the *Staphylococcus aureus* enterotoxin proteins is present in the vaccine composition in an amount of 50 µg to 200 µg and each of the *Staphylococcus aureus* cytotoxin proteins are present in the vaccine composition in an amount of 50 µg to 200 µg.

6. The vaccine composition according to claim 3, further comprising an aluminum hydroxide gel.

7. The *Staphylococcus aureus* enterotoxin protein according to claim 1, wherein the protein comprises the amino acid sequence represented by SEQ ID NO: 2.

8. The *Staphylococcus aureus* enterotoxin protein according to claim 1, wherein the protein comprises the amino acid sequence represented by SEQ ID NO: 4.

9. The *Staphylococcus aureus* enterotoxin protein according to claim 1, wherein the protein comprises the amino acid sequence represented by SEQ ID NO: 6.

10. The *Staphylococcus aureus* enterotoxin protein according to claim 1, wherein the protein comprises the amino acid sequence represented by SEQ ID NO: 8.

11. The *Staphylococcus aureus* enterotoxin protein according to claim 1, wherein the protein comprises the amino acid sequence represented by SEQ ID NO: 10.

12. The vaccine composition according to claim 3, wherein each of the *Staphylococcus aureus* enterotoxin proteins is present in the vaccine composition in an amount of 50 µg to 150 µg and each of the *Staphylococcus aureus* cytotoxin proteins is present in the vaccine composition in an amount of 50 µg to 150 µg.

13. The vaccine composition according to claim 3, wherein each of the *Staphylococcus aureus* enterotoxin proteins is present in the vaccine composition in an amount of 50 µg to 100 µg and each of the *Staphylococcus aureus* cytotoxin proteins is present in the vaccine composition in an amount of 50 µg to 100 µg.

14. The vaccine composition according to claim 3, wherein the *Staphylococcus aureus* enterotoxin proteins and the *Staphylococcus aureus* cytotoxin proteins are present in the vaccine composition in a ratio of 1:0.75 to 1:1 (w/w).

15. A vaccine composition for preventing bovine mastitis, the vaccine composition comprising five *Staphylococcus aureus* enterotoxin proteins represented by SEQ ID NO: 2, SEQ ID NO: 4; SEQ ID NO: 6, SEQ ID NO: 8 and SEQ ID NO: 10 and four *Staphylococcus aureus* cytotoxin proteins represented by SEQ ID NO: 15, SEQ ID NO: 19, SEQ ID NO: 23 and SEQ ID NO: 27.

16. The vaccine composition according to claim 15, wherein the *Staphylococcus aureus* enterotoxin proteins and the *Staphylococcus aureus* cytotoxin proteins present in the vaccine composition in a ratio of 1:0.5 to 1:1.5 (w/w).

17. The vaccine composition according to claim 15, wherein each of the *Staphylococcus aureus* enterotoxin proteins is present in the vaccine composition in an amount of 50 μg to 200 μg and each of the *Staphylococcus aureus* cytotoxin proteins are present in the vaccine composition in an amount of 50 μg to 150 μg.

18. The vaccine composition according to claim 15, wherein each of the *Staphylococcus aureus* enterotoxin proteins is present in the vaccine composition in an amount of 50 μg to 100 μg and each of the *Staphylococcus aureus* cytotoxin proteins is present in the vaccine composition in an amount of 50 μg to 100 μg.

* * * * *

SEQUENCE LISTING

```
<160> NUMBER OF SEQ ID NOS: 27

<210> SEQ ID NO 1
<211> LENGTH: 702
<212> TYPE: DNA
<213> ORGANISM: Artificial Sequence
<220> FEATURE:
<223> OTHER INFORMATION: Mutant SEG

<400> SEQUENCE: 1
caacccgatc ctaaattaga cgaactaaat aaagtaagtg attataaaaa taataaggga      60
actatgggtg ctgtaatgaa tctttatacg tctccacctg ttgaaggaag aggagttatt     120
aattctagac agttttttatc tcatgattta attttttccaa ttgagtataa gagttataat     180
gaggttaaaa ctgaattaga aaatacagaa ttagctaaca attataaaga taaaaaagta     240
gacatttttg gcgttccata tttttataca tgtataatac ctaaatctga accggatata     300
aaccaaaatt ttggaggttg ttgtatgtat ggtggtctta catttaatag ttcagaaaat     360
gaaagagata aattaattac tgtacaggta acaatcgaca atagacaatc acttggattt     420
acaataacta caaataagaa tatggttact attcaggaac tagattacaa agcaagacac     480
tggctcacta aagaaaaaaa gctatacgag gctgctggtt ctgcatttga atctggatat     540
ataaaattta ctgaaaagaa caatacaagt ttttggtttg acttatttcc taaaaaagaa     600 ctagtaccctt ttgttccata taagttttta aatatttacg gagataataa agttgttgat     660
tctaagagta ttaaaatgga agtatttctt aatactcact ga                        702

<210> SEQ ID NO 2
<211> LENGTH: 233
<212> TYPE: PRT
<213> ORGANISM: Artificial Sequence
<220> FEATURE:
<223> OTHER INFORMATION: Mutant SEG

<400> SEQUENCE: 2

Gln Pro Asp Pro Lys Leu Asp Glu Leu Asn Lys Val Ser Asp Tyr Lys
1               5                   10                  15

Asn Asn Lys Gly Thr Met Gly Ala Val Met Asn Leu Tyr Thr Ser Pro
            20                  25                  30

Pro Val Glu Gly Arg Gly Val Ile Asn Ser Arg Gln Phe Leu Ser His
        35                  40                  45

Asp Leu Ile Phe Pro Ile Glu Tyr Lys Ser Tyr Asn Glu Val Lys Thr
    50                  55                  60

Glu Leu Glu Asn Thr Glu Leu Ala Asn Asn Tyr Lys Asp Lys Lys Val
65                  70                  75                  80

Asp Ile Phe Gly Val Pro Tyr Phe Tyr Thr Cys Ile Ile Pro Lys Ser
                85                  90                  95

Glu Pro Asp Ile Asn Gln Asn Phe Gly Gly Cys Cys Met Tyr Gly Gly
```

```
            100                 105                 110
Leu Thr Phe Asn Ser Ser Glu Asn Glu Arg Asp Lys Leu Ile Thr Val
            115                 120                 125

Gln Val Thr Ile Asp Asn Arg Gln Ser Leu Gly Phe Thr Ile Thr Thr
            130                 135                 140

Asn Lys Asn Met Val Thr Ile Gln Glu Leu Asp Tyr Lys Ala Arg His
145                 150                 155                 160

Trp Leu Thr Lys Glu Lys Lys Leu Tyr Glu Ala Ala Gly Ser Ala Phe
                165                 170                 175

Glu Ser Gly Tyr Ile Lys Phe Thr Glu Lys Asn Asn Thr Ser Phe Trp
                180                 185                 190

Phe Asp Leu Phe Pro Lys Lys Glu Leu Val Pro Phe Val Pro Tyr Lys
            195                 200                 205

Phe Leu Asn Ile Tyr Gly Asp Asn Lys Val Val Asp Ser Lys Ser Ile
            210                 215                 220

Lys Met Glu Val Phe Leu Asn Thr His
225                 230
```

<210> SEQ ID NO 3
<211> LENGTH: 651
<212> TYPE: DNA
<213> ORGANISM: Artificial Sequence
<220> FEATURE:
<223> OTHER INFORMATION: Mutant SEI

<400> SEQUENCE: 3

```
gatattggtg taggtaactt aagaaatttc tatacaaaac atgattatat agatttaaaa    60
ggcgtcacag ataaaaacct acctattgca aatcaactcg aattttcaac aggtaccaat   120
gatttgatct cagaatctaa taattgggac gaaataagta aatttaaagg aaagaaactg   180
gatattttg gcattgatta taatggtcct tgtaaatcta aatacatgta tggaggggcc    240
actttatcag acaatactt aaattctgct agaaaaatcc ctattaatct ttgggttaat    300
ggcaaacata aacaatttc tactgacaaa atagcaacta taaaaaaact agtaacagct    360
caagaaattg atgttaaatt aagaagatat cttcaagaag aatacaatat atatggtaat    420
aataacactg gtaaaggcaa agaatatgga tataaatcta aattttattc aggttttaat    480
aatgggaaag ttttatttca tttaaataat gaaaaatcat tttcatatga tttgttttat    540
acaggagatg gactgcctgt aagttttttg aaaatttatg aagataataa aataatagaa    600
tctgaaaaat ttgctcttgc tgtcgaaata tcatatgtag atagtaacta a             651
```

<210> SEQ ID NO 4
<211> LENGTH: 216
<212> TYPE: PRT
<213> ORGANISM: Artificial Sequence
<220> FEATURE:
<223> OTHER INFORMATION: Mutant SEI

<400> SEQUENCE: 4

```
Asp Ile Gly Val Gly Asn Leu Arg Asn Phe Tyr Thr Lys His Asp Tyr
1               5                   10                  15

Ile Asp Leu Lys Gly Val Thr Asp Lys Asn Leu Pro Ile Ala Asn Gln
            20                  25                  30

Leu Glu Phe Ser Thr Gly Thr Asn Asp Leu Ile Ser Glu Ser Asn Asn
        35                  40                  45

Trp Asp Glu Ile Ser Lys Phe Lys Gly Lys Lys Leu Asp Ile Phe Gly
    50                  55                  60
```

Ile Asp Tyr Asn Gly Pro Cys Lys Ser Lys Tyr Met Tyr Gly Gly Ala
65                  70                  75                  80

Thr Leu Ser Gly Gln Tyr Leu Asn Ser Ala Arg Lys Ile Pro Ile Asn
            85                  90                  95

Leu Trp Val Asn Gly Lys His Lys Thr Ile Ser Thr Asp Lys Ile Ala
            100                 105                 110

Thr Asn Lys Lys Leu Val Thr Ala Gln Glu Ile Asp Val Lys Leu Arg
            115                 120                 125

Arg Tyr Leu Gln Glu Glu Tyr Asn Ile Tyr Gly Asn Asn Thr Gly
        130                 135                 140

Lys Gly Lys Glu Tyr Gly Tyr Lys Ser Lys Phe Tyr Ser Gly Phe Asn
145                 150                 155                 160

Asn Gly Lys Val Leu Phe His Leu Asn Asn Glu Lys Ser Phe Ser Tyr
            165                 170                 175

Asp Leu Phe Tyr Thr Gly Asp Gly Leu Pro Val Ser Phe Leu Lys Ile
            180                 185                 190

Tyr Glu Asp Asn Lys Ile Ile Glu Ser Glu Lys Phe Ala Leu Ala Val
        195                 200                 205

Glu Ile Ser Tyr Val Asp Ser Asn
    210                 215

<210> SEQ ID NO 5
<211> LENGTH: 654
<212> TYPE: DNA
<213> ORGANISM: Artificial Sequence
<220> FEATURE:
<223> OTHER INFORMATION: Mutant SEM

<400> SEQUENCE: 5
gatgtcggag ttttgactct taggaactat tatggtagct atccaattga agaccaccaa      60
agtattaatc ctgaaaataa tcatctttcg catcaattag ttttttctat ggataattcg     120
acagtaacag ctgaatttaa gaacgttgat gatgtaaaga aattcaaaaa tcatgctgta     180
gatgtatatg gtctaagtta tagtggatat tgtttgaaaa acaaatatat atacggtgga     240
gttacattag caggtgatta tttagagaaa tctagacgta ttcctattaa tctttgggtt     300
aatggagaac atcaaactat atctactgac aaagtatcaa ctaataaaaa gttagtaaca     360
gctcaagaaa ttgatactaa attaagaaga tatctacaag aagaatataa tatttatggc     420
tttaatgata caaataaagg aagaaattat ggtaataagt caaaatttag ttctggattt     480
aatgcaggaa aaatattatt tcatttgaat gatggttcat cattttctta tgacttattt     540
gatactggaa caggacaagc tgaaagtttc ttaaaaatat ataatgacaa caaaactgtc     600
gaaactgaaa aattcgcttt agctgtagaa atatcttata aggacgaaag ttga           654

<210> SEQ ID NO 6
<211> LENGTH: 217
<212> TYPE: PRT
<213> ORGANISM: Artificial Sequence
<220> FEATURE:
<223> OTHER INFORMATION: Mutant SEM

<400> SEQUENCE: 6

Asp Val Gly Val Leu Thr Leu Arg Asn Tyr Tyr Gly Ser Tyr Pro Ile
1               5                   10                  15

Glu Asp His Gln Ser Ile Asn Pro Glu Asn Asn His Leu Ser His Gln
            20                  25                  30

Leu Val Phe Ser Met Asp Asn Ser Thr Val Thr Ala Glu Phe Lys Asn
            35                  40                  45

Val Asp Asp Val Lys Lys Phe Lys Asn His Ala Val Asp Val Tyr Gly
 50                  55                  60

Leu Ser Tyr Ser Gly Tyr Cys Leu Lys Asn Lys Tyr Ile Tyr Gly Gly
 65                  70                  75                  80

Val Thr Leu Ala Gly Asp Tyr Leu Glu Lys Ser Arg Arg Ile Pro Ile
                 85                  90                  95

Asn Leu Trp Val Asn Gly Glu His Gln Thr Ile Ser Thr Asp Lys Val
            100                 105                 110

Ser Thr Asn Lys Lys Leu Val Thr Ala Gln Glu Ile Asp Thr Lys Leu
            115                 120                 125

Arg Arg Tyr Leu Gln Glu Glu Tyr Asn Ile Tyr Gly Phe Asn Asp Thr
130                 135                 140

Asn Lys Gly Arg Asn Tyr Gly Asn Lys Ser Lys Phe Ser Ser Gly Phe
145                 150                 155                 160

Asn Ala Gly Lys Ile Leu Phe His Leu Asn Asp Gly Ser Ser Phe Ser
                165                 170                 175

Tyr Asp Leu Phe Asp Thr Gly Thr Gly Gln Ala Glu Ser Phe Leu Lys
            180                 185                 190

Ile Tyr Asn Asp Asn Lys Thr Val Glu Thr Glu Lys Phe Ala Leu Ala
            195                 200                 205

Val Glu Ile Ser Tyr Lys Asp Glu Ser
    210                 215

<210> SEQ ID NO 7
<211> LENGTH: 684
<212> TYPE: DNA
<213> ORGANISM: Artificial Sequence
<220> FEATURE:
<223> OTHER INFORMATION: Mutant SEN

<400> SEQUENCE: 7
gaagtagaca aaaagatttt aaagaaaaaa tctgatctag atagtagtaa gttatttaat      60
ttaacaagct attatactga tataacgtgg caattagacg agtcaaataa aattagtaca     120
gatcaactac tgaataatac tataatatta aaaaatattg atatatccgt acttaaaact     180
tctagtttga agttgagtt taactcatca gatttagcaa atcaatttaa aggaaaaaat      240
atagatattt atggactgta ttttggaaat aaatgtgtag gcttaactga agaaaaaaca     300
tcatgcttat acggaggagt tacgatacat gatggaaatc aattagatga agagaaagtt     360
ataggcgtta atgtatttaa agatggtgtc caacaagaag ttttgttat aaaaaccaaa     420 aaggctaaag taacagtaca agaattagac actaaagttc gatttaaatt agaaaatttta   480 tataaaatat acaataaaga taccggtaac atacaaaaag gatgcatttt cttcattct    540 cataatcatc aagatcaatc attttattat gatttatata acgtaaaagg ttcagtggga    600
gcagagtttt ttcaattta tagtgataat agaacagtta gctcatctaa ttatgctatt    660
gctgtatttt tatataaaga ttaa                                           684

<210> SEQ ID NO 8
<211> LENGTH: 227
<212> TYPE: PRT
<213> ORGANISM: Artificial Sequence
<220> FEATURE:
<223> OTHER INFORMATION: Mutant SEN

<400> SEQUENCE: 8

```
Glu Val Asp Lys Lys Asp Leu Lys Lys Ser Asp Leu Asp Ser Ser
1               5                   10                  15

Lys Leu Phe Asn Leu Thr Ser Tyr Tyr Thr Asp Ile Thr Trp Gln Leu
            20                  25                  30

Asp Glu Ser Asn Lys Ile Ser Thr Asp Gln Leu Leu Asn Asn Thr Ile
                35                  40                  45

Ile Leu Lys Asn Ile Asp Ile Ser Val Leu Lys Thr Ser Ser Leu Lys
50                  55                  60

Val Glu Phe Asn Ser Ser Asp Leu Ala Asn Gln Phe Lys Gly Lys Asn
65                  70                  75                  80

Ile Asp Ile Tyr Gly Leu Tyr Phe Gly Asn Lys Cys Val Gly Leu Thr
                85                  90                  95

Glu Glu Lys Thr Ser Cys Leu Tyr Gly Gly Val Thr Ile His Asp Gly
                100                 105                 110

Asn Gln Leu Asp Glu Glu Lys Val Ile Gly Val Asn Val Phe Lys Asp
            115                 120                 125

Gly Val Gln Gln Glu Gly Phe Val Ile Lys Thr Lys Lys Ala Lys Val
        130                 135                 140

Thr Val Gln Glu Leu Asp Thr Lys Val Arg Phe Lys Leu Glu Asn Leu
145                 150                 155                 160

Tyr Lys Ile Tyr Asn Lys Asp Thr Gly Asn Ile Gln Lys Gly Cys Ile
                165                 170                 175

Phe Phe His Ser His Asn His Gln Asp Gln Ser Phe Tyr Tyr Asp Leu
            180                 185                 190

Tyr Asn Val Lys Gly Ser Val Gly Ala Glu Phe Gln Phe Tyr Ser
        195                 200                 205

Asp Asn Arg Thr Val Ser Ser Ser Asn Tyr Ala Ile Ala Val Phe Leu
210                 215                 220

Tyr Lys Asp
225

<210> SEQ ID NO 9
<211> LENGTH: 699
<212> TYPE: DNA
<213> ORGANISM: Artificial Sequence
<220> FEATURE:
<223> OTHER INFORMATION: Mutant SEO

<400> SEQUENCE: 9
aatgaagaag atcctaaaat agagagtttg tgtaagaagt caagtgtaga ccctattgct    60
ttacataata ttaatgatga ttatataaat aatcgattta cgacagtaaa atcaattgta   120
tcaactacag aaaaattctt agacttcgat ttattattta aagtattaa ttggttagat    180 ggaatatctg ctgaatttaa agatttaaaa gtggaattta gctcatcagc gatttctaaa   240
gaatttctag aaagactgt tgatatttat ggtgtttact ataaagcaca ttgtcgtggt    300
gagcatcaag tggatactgc ctgtacatat ggtggggtaa caccctcatga aaataataaa   360 ttaagcgagc ctaaaaatat aggagtagct gtgtataagg ataatgtaaa tgttaataca   420
tttatcgtta ctacagataa aaagaaagtt actgcacaag aacttgatat taaagtaaga   480
acaaaattaa ataatgcata taattgtat gacagaatga ctagtgatgt acaaaaaggt   540
tatattaaat ttcattctca ttcggagcat aaagaatcat tttattatga tttatttat    600 attaaaggaa atttaccaga tcaatatttg caaatttata atgataataa aacaatagat   660
tcatcagact atgctattgc tgtttattta tttacataa                            699
```

<210> SEQ ID NO 10
<211> LENGTH: 232
<212> TYPE: PRT
<213> ORGANISM: Artificial Sequence
<220> FEATURE:
<223> OTHER INFORMATION: Mutant SEO

<400> SEQUENCE: 10

```
Asn Glu Glu Asp Pro Lys Ile Glu Ser Leu Cys Lys Lys Ser Val
1               5                   10                  15

Asp Pro Ile Ala Leu His Asn Ile Asn Asp Asp Tyr Ile Asn Asn Arg
            20                  25                  30

Phe Thr Thr Val Lys Ser Ile Val Ser Thr Thr Glu Lys Phe Leu Asp
                35                  40                  45

Phe Asp Leu Leu Phe Lys Ser Ile Asn Trp Leu Asp Gly Ile Ser Ala
    50                  55                  60

Glu Phe Lys Asp Leu Lys Val Glu Phe Ser Ser Ser Ala Ile Ser Lys
65                  70                  75                  80

Glu Phe Leu Gly Lys Thr Val Asp Ile Tyr Gly Val Tyr Lys Ala
                85                  90                  95

His Cys Arg Gly Glu His Gln Val Asp Thr Ala Cys Thr Tyr Gly Gly
            100                 105                 110

Val Thr Pro His Glu Asn Asn Lys Leu Ser Glu Pro Lys Asn Ile Gly
                115                 120                 125

Val Ala Val Tyr Lys Asp Asn Val Asn Val Asn Thr Phe Ile Val Thr
    130                 135                 140

Thr Asp Lys Lys Lys Val Thr Ala Gln Glu Leu Asp Ile Lys Val Arg
145                 150                 155                 160

Thr Lys Leu Asn Asn Ala Tyr Lys Leu Tyr Asp Arg Met Thr Ser Asp
                165                 170                 175

Val Gln Lys Gly Tyr Ile Lys Phe His Ser His Ser Glu His Lys Glu
            180                 185                 190

Ser Phe Tyr Tyr Asp Leu Phe Tyr Ile Lys Gly Asn Leu Pro Asp Gln
                195                 200                 205

Tyr Leu Gln Ile Tyr Asn Asp Asn Lys Thr Ile Asp Ser Ser Asp Tyr
    210                 215                 220

Ala Ile Ala Val Tyr Leu Phe Thr
225                 230
```

<210> SEQ ID NO 11
<211> LENGTH: 242
<212> TYPE: DNA
<213> ORGANISM: Artificial Sequence
<220> FEATURE:
<223> OTHER INFORMATION: ETA promoter

<400> SEQUENCE: 11

```
aaatatcaac gtgagggctc tagtactaac gattttttt gtgcagtatg tagaatcact      60
gacaaggaac aaaagattaa aaatgaaaaa tattggggaa ctattgagtg gaattaacaa    120
acgtatttaa tgtttagtta attaaaagtt aataaaaaat aatttgtttt gaaatagaaa    180
cgttatataa tttttaatgt attcgaatac attaaaaaac gcaaatgtta ggatgattaa    240
ta                                                                   242
```

<210> SEQ ID NO 12
<211> LENGTH: 87

```
<212> TYPE: DNA
<213> ORGANISM: Artificial Sequence
<220> FEATURE:
<223> OTHER INFORMATION: HlgA signal peptide

<400> SEQUENCE: 12
atgattaaaa ataaaatatt aacagcaact ttagcagttg gtttaatagc ccctttagcc    60
aatccattta tagaaatttc taaagca                                       87

<210> SEQ ID NO 13
<211> LENGTH: 843
<212> TYPE: DNA
<213> ORGANISM: Artificial Sequence
<220> FEATURE:
<223> OTHER INFORMATION: HlgA mature protein

<400> SEQUENCE: 13
gaaaataaga tagaagatat cggccaaggt gcagaaatca tcaaaagaac acaagacatt    60
actagcaaac gattagctat aactcaaaac attcaatttg attttgtaaa agataaaaaa   120
tataacaaag atgccctagt tgttaagatg caaggcttca ttagctctag aacaacatat   180
tcagacttaa aaaatatcc atatattaaa agaatgatat ggccatttca atataatatc    240
agtttgaaaa cgaaagactc taatgttgat ttaattaatt atcttcctaa aaataaaatt   300
gattcagcag atgttagtca gaaattaggc tataatatcg gcggaaactt ccaatcagcg   360
ccatcaatcg gaggcagtgg ctcattcaac tactctaaaa caattagtta taatcaaaaa   420
aactatgtta ctgaagtaga aagtcagaac tctaaaggtg ttaaatgggg agtgaaagca   480
aattcattcg ttacaccgaa tggtcaagta tctgcatatg atcaatactt atttgcacaa   540
gacccaactg gtccagcagc acgagactat ttcgtcccag ataatcaact acctcctta   600 attcaaagtg gctttaatcc atcatttatt acaacattgt cacacgaaag aggtaaaggt   660
gataaaagcg agtttgaaat cacttacggc agaaacatgg atgctacata tgcttacgtg   720
acaagacatc gtttagccgt tgatagaaaa catgatgctt taaaaaccg aaacgttaca   780 gttaaatatg aagtgaactg gaaaacacat gaagtaaaaa ttaaaagcat cacacctaag   840
taa                                                                 843

<210> SEQ ID NO 14
<211> LENGTH: 1172
<212> TYPE: DNA
<213> ORGANISM: Artificial Sequence
<220> FEATURE:
<223> OTHER INFORMATION: ETA-Hlg

<400> SEQUENCE: 14
aaatatcaac gtgagggctc tagtactaac gatttttttt gtgcagtatg tagaatcact    60
gacaaggaac aaaagattaa aaatgaaaaa tattggggaa ctattgagtg gaattaacaa   120
acgtatttaa tgtttagtta attaaaagtt aataaaaaat aatttgtttt gaaatagaaa   180
cgttatataa ttttttaatgt attcgaatac attaaaaaac gcaaatgtta ggatgattaa   240
taatgattaa aaataaaata ttaacagcaa ctttagcagt tggtttaata gcccctttag   300
ccaatccatt tatagaaatt tctaaagcag aaaataagat agaagatatc ggccaaggtg   360
cagaaatcat caaaagaaca caagacatta ctagcaaacg attagctata actcaaaaca   420
ttcaatttga ttttgtaaaa gataaaaaat ataacaaaga tgccctagtt gttaagatgc   480
aaggcttcat tagctctaga acaacatatt cagacttaaa aaaatatcca tatattaaaa   540
```

```
gaatgatatg gccatttcaa tataatatca gtttgaaaac gaaagactct aatgttgatt      600
taattaatta tcttcctaaa aataaaattg attcagcaga tgttagtcag aaattaggct      660
ataatatcgg cggaaacttc caatcagcgc catcaatcgg aggcagtggc tcattcaact      720
actctaaaac aattagttat aatcaaaaaa actatgttac tgaagtagaa agtcagaact      780
ctaaaggtgt taaatgggga gtgaaagcaa attcattcgt tacaccgaat ggtcaagtat      840
ctgcatatga tcaatactta tttgcacaag acccaactgg tccagcagca cgagactatt      900
tcgtcccaga taatcaacta cctcctttaa ttcaaagtgg ctttaatcca tcatttatta      960
caacattgtc acacgaaaga ggtaaaggtg ataaaagcga gtttgaaatc acttacggca     1020
gaaacatgga tgctacatat gcttacgtga caagacatcg tttagccgtt gatagaaaac     1080
atgatgcttt taaaaaccga aacgttacag ttaaatatga agtgaactgg aaaacacatg     1140
aagtaaaaat taaaagcatc acacctaagt aa                                   1172
```

<210> SEQ ID NO 15
<211> LENGTH: 280
<212> TYPE: PRT
<213> ORGANISM: Artificial Sequence
<220> FEATURE:
<223> OTHER INFORMATION: HlgA

<400> SEQUENCE: 15

```
Glu Asn Lys Ile Glu Asp Ile Gly Gln Gly Ala Glu Ile Ile Lys Arg
1               5                   10                  15

Thr Gln Asp Ile Thr Ser Lys Arg Leu Ala Ile Thr Gln Asn Ile Gln
                20                  25                  30

Phe Asp Phe Val Lys Asp Lys Tyr Asn Lys Asp Ala Leu Val Val
            35                  40                  45

Lys Met Gln Gly Phe Ile Ser Ser Arg Thr Thr Tyr Ser Asp Leu Lys
 50                  55                  60

Lys Tyr Pro Tyr Ile Lys Arg Met Ile Trp Pro Phe Gln Tyr Asn Ile
 65                  70                  75                  80

Ser Leu Lys Thr Lys Asp Ser Asn Val Asp Leu Ile Asn Tyr Leu Pro
                 85                  90                  95

Lys Asn Lys Ile Asp Ser Ala Asp Val Ser Gln Lys Leu Gly Tyr Asn
                100                 105                 110

Ile Gly Gly Asn Phe Gln Ser Ala Pro Ser Ile Gly Gly Ser Gly Ser
            115                 120                 125

Phe Asn Tyr Ser Lys Thr Ile Ser Tyr Asn Gln Lys Asn Tyr Val Thr
130                 135                 140

Glu Val Glu Ser Gln Asn Ser Lys Gly Val Lys Trp Gly Val Lys Ala
145                 150                 155                 160

Asn Ser Phe Val Thr Pro Asn Gly Gln Val Ser Ala Tyr Asp Gln Tyr
                165                 170                 175

Leu Phe Ala Gln Asp Pro Thr Gly Pro Ala Ala Arg Asp Tyr Phe Val
            180                 185                 190

Pro Asp Asn Gln Leu Pro Pro Leu Ile Gln Ser Gly Phe Asn Pro Ser
        195                 200                 205

Phe Ile Thr Thr Leu Ser His Glu Arg Gly Lys Gly Asp Lys Ser Glu
210                 215                 220

Phe Glu Ile Thr Tyr Gly Arg Asn Met Asp Ala Thr Tyr Ala Tyr Val
225                 230                 235                 240

Thr Arg His Arg Leu Ala Val Asp Arg Lys His Asp Ala Phe Lys Asn
                245                 250                 255
```

Arg Asn Val Thr Val Lys Tyr Glu Val Asn Trp Lys Thr His Glu Val
260 265 270

Lys Ile Lys Ser Ile Thr Pro Lys
275 280

<210> SEQ ID NO 16
<211> LENGTH: 87
<212> TYPE: DNA
<213> ORGANISM: Artificial Sequence
<220> FEATURE:
<223> OTHER INFORMATION: H1gC signal peptide

<400> SEQUENCE: 16
atgcttaaaa ataaaatatt aactacaact ttatctgtga gcttacttgc ccctcttgcc 60
aatccgttat tagaaaatgc taaagct 87

<210> SEQ ID NO 17
<211> LENGTH: 861
<212> TYPE: DNA
<213> ORGANISM: Artificial Sequence
<220> FEATURE:
<223> OTHER INFORMATION: HlgC mature protein

<400> SEQUENCE: 17
gctaacgata ctgaagacat cggtaaagga agcgatatag aaattatcaa aaggacagaa 60
gataaaacaa gtaataaatg gggcgtgact caaaatattc aatttgattt tgtaaaggat 120
aaaaaatata acaaagatgc tttgatatta aagatgcaag gattcattag ctctagaaca 180
acatattaca actataaaaa aactaatcat gttaaagcta tgcgatggcc attccaatat 240
aatattggtt taaaaacaaa tgataaatat gtttctttaa ttaattattt acctaaaaat 300
aaaattgaat ctacaaacgt gagtcagaca ttaggataca atatcggtgg taatttccaa 360
tcagccccat cactcggtgg taatggatca tttaactatt ctaaatcgat tagctataca 420
caacaaaatt atgtaagtga agtagaacaa caaaactcaa aaagtgtttt atggggcgtc 480
aaagcgaatt cattcgccac tgaatcaggt caaaaatcag cctttgatag cgatttattt 540
gtaggctaca aacctcatag taaagatcct agagattatt tcgttccaga cagtgagtta 600
ccacctcttg tacaaagtgg atttaaccct tcatttatcg ccacagtatc tcatgaaaaa 660
ggttcaagcg atacaagcga atttgaaatt acttacggaa gaaacatgga tgtcactcat 720
gccattaaaa gatcaacgca ttatggcaac agttatttag acggacatag agtccataat 780
gcatttgtaa atagaaacta tactgtgaaa tacgaggtca attggaagac tcatgaaatc 840
aaggtgaaag gacagaattg a 861

<210> SEQ ID NO 18
<211> LENGTH: 1190
<212> TYPE: DNA
<213> ORGANISM: Artificial Sequence
<220> FEATURE:
<223> OTHER INFORMATION: ETA-HlgC

<400> SEQUENCE: 18
aaatatcaac gtgagggctc tagtactaac gatttttttt gtgcagtatg tagaatcact 60
gacaaggaac aaaagattaa aaatgaaaaa tattggggaa ctattgagtg gaattaacaa 120
acgtatttaa tgtttagtta attaaaagtt aataaaaaat aatttgtttt gaaatagaaa 180
cgttatataa tttttaatgt attcgaatac attaaaaaac gcaaatgtta ggatgattaa 240

```
taatgcttaa aaataaaata ttaactacaa ctttatctgt gagcttactt gcccctcttg    300
ccaatccgtt attagaaaat gctaaagctg ctaacgatac tgaagacatc ggtaaaggaa    360
gcgatataga aattatcaaa aggacagaag ataaaacaag taataaatgg ggcgtgactc    420
aaaatattca atttgatttt gtaaaggata aaaaatataa caaagatgct ttgatattaa    480
agatgcaagg attcattagc tctagaacaa catattacaa ctataaaaaa actaatcatg    540
ttaaagctat gcgatggcca ttccaatata atattggttt aaaaacaaat gataaatatg    600
tttctttaat taattattta cctaaaaata aaattgaatc tacaaacgtg agtcagacat    660
taggatacaa tatcggtggt aatttccaat cagccccatc actcggtggt aatggatcat    720
ttaactattc taaatcgatt agctatacac aacaaaatta tgtaagtgaa gtagaacaac    780
aaaactcaaa aagtgtttta tggggcgtca aagcgaattc attcgccact gaatcaggtc    840
aaaaatcagc ctttgatagc gatttatttg taggctacaa acctcatagt aaagatccta    900
gagattattt cgttccagac agtgagttac cacctcttgt acaaagtgga tttaacccctt    960 catttatcgc cacagtatct catgaaaaag gttcaagcga tacaagcgaa tttgaaatta   1020
cttacggaag aaacatggat gtcactcatg ccattaaaag atcaacgcat tatggcaaca   1080
gttatttaga cggacataga gtccataatg catttgtaaa tagaaactat actgtgaaat   1140
acgaggtcaa ttggaagact catgaaatca aggtgaaagg acagaattga              1190
```

<210> SEQ ID NO 19
<211> LENGTH: 286
<212> TYPE: PRT
<213> ORGANISM: Artificial Sequence
<220> FEATURE:
<223> OTHER INFORMATION: HlgC

<400> SEQUENCE: 19

```
Ala Asn Asp Thr Glu Asp Ile Gly Lys Gly Ser Asp Ile Glu Ile Ile
1               5                   10                  15

Lys Arg Thr Glu Asp Lys Thr Ser Asn Lys Trp Gly Val Thr Gln Asn
            20                  25                  30

Ile Gln Phe Asp Phe Val Lys Asp Lys Lys Tyr Asn Lys Asp Ala Leu
        35                  40                  45

Ile Leu Lys Met Gln Gly Phe Ile Ser Ser Arg Thr Thr Tyr Tyr Asn
    50                  55                  60

Tyr Lys Lys Thr Asn His Val Lys Ala Met Arg Trp Pro Phe Gln Tyr
65                  70                  75                  80

Asn Ile Gly Leu Lys Thr Asn Asp Lys Tyr Val Ser Leu Ile Asn Tyr
                85                  90                  95

Leu Pro Lys Asn Lys Ile Glu Ser Thr Asn Val Ser Gln Thr Leu Gly
            100                 105                 110

Tyr Asn Ile Gly Gly Asn Phe Gln Ser Ala Pro Ser Leu Gly Gly Asn
        115                 120                 125

Gly Ser Phe Asn Tyr Ser Lys Ser Ile Ser Tyr Thr Gln Gln Asn Tyr
    130                 135                 140

Val Ser Glu Val Glu Gln Gln Asn Ser Lys Ser Val Leu Trp Gly Val
145                 150                 155                 160

Lys Ala Asn Ser Phe Ala Thr Glu Ser Gly Gln Lys Ser Ala Phe Asp
                165                 170                 175

Ser Asp Leu Phe Val Gly Tyr Lys Pro His Ser Lys Asp Pro Arg Asp
            180                 185                 190

Tyr Phe Val Pro Asp Ser Glu Leu Pro Pro Leu Val Gln Ser Gly Phe
```

```
              195                 200                 205
Asn Pro Ser Phe Ile Ala Thr Val Ser His Glu Lys Gly Ser Ser Asp
    210                 215                 220

Thr Ser Glu Phe Glu Ile Thr Tyr Gly Arg Asn Met Asp Val Thr His
225                 230                 235                 240

Ala Ile Lys Arg Ser Thr His Tyr Gly Asn Ser Tyr Leu Asp Gly His
                245                 250                 255

Arg Val His Asn Ala Phe Val Asn Arg Asn Tyr Thr Val Lys Tyr Glu
            260                 265                 270

Val Asn Trp Lys Thr His Glu Ile Lys Val Lys Gly Gln Asn
        275                 280                 285

<210> SEQ ID NO 20
<211> LENGTH: 84
<212> TYPE: DNA
<213> ORGANISM: Artificial Sequence
<220> FEATURE:
<223> OTHER INFORMATION: LukE signal peptide

<400> SEQUENCE: 20
atgtttaaga aaaaaatgtt agctgcaact ttgtcagtag gactgattgc acctttagca     60
tctccgattc aagaatctag agca                                            84

<210> SEQ ID NO 21
<211> LENGTH: 852
<212> TYPE: DNA
<213> ORGANISM: Artificial Sequence
<220> FEATURE:
<223> OTHER INFORMATION: LukE mature protein

<400> SEQUENCE: 21
aatactaata ttgaaaatat tggtgatggt gctgaagtaa tcaaacgtac ggaggatgta     60
agtagtaaga atggggcgt tactcaaaat gtccaattcg actttgtaaa agataaaaaa    120
tataacaaag acgctttaat tgttaaaatg caaggtttta ttaattccag aacttcattt    180
tcagatgtga agggtagtgg atatgaatta actaaacgaa tgatttggcc attccaatat    240
aatataggac tgacgactaa agatccaaat gttagcttaa tcaattacct tcctaaaaac    300
aaaatagaaa ctactgatgt tggtcaaaca ttaggatata acattggagg taatttccag    360
tcagcaccat ctataggtgg caatggctca tttaattatt ctaaaacaat tagttatacc    420
caaaagagtt atgtcagtga agtagacaag caaaactcaa aatctgttaa atggggtgtt    480
aaagcaaacg aatttgttac gcctgatgga aaaaaatctg cgcatgatag atatttattc    540
gtacaaagtc caaatggtcc aacaggttca gcaagagaat attttgctcc tgataatcaa    600
ttgccacctt tagttcaaag tggctttaat ccatcgttta tcactacact atcacatgaa    660
aaaggttcaa gtgatacgag tgaatttgaa atttcatatg gtagaaactt agatattaca    720
tatgcgactt tattccctag aactggtatt tacgcagaaa gaaagcataa tgcatttgta    780
aatagaaact tgtagttag atatgaagtt aattggaaaa cacacgaaat taaagtgaaa    840
ggacataatt aa                                                        852

<210> SEQ ID NO 22
<211> LENGTH: 1178
<212> TYPE: DNA
<213> ORGANISM: Artificial Sequence
<220> FEATURE:
<223> OTHER INFORMATION: ETA-LukE
```

-continued

<400> SEQUENCE: 22

```
aaatatcaac gtgagggctc tagtactaac gattttttt gtgcagtatg tagaatcact       60
gacaaggaac aaaagattaa aaatgaaaaa tattggggaa ctattgagtg gaattaacaa      120
acgtatttaa tgtttagtta attaaaagtt aataaaaaat aatttgtttt gaaatagaaa      180
cgttatataa ttttttaatgt attcgaatac attaaaaaac gcaaatgtta ggatgattaa    240
taatgtttaa gaaaaaaatg ttagctgcaa ctttgtcagt aggactgatt gcaccttag     300
catctccgat tcaagaatct agagcaaata ctaatattga aatattggt gatggtgctg     360
aagtaatcaa acgtacggag gatgtaagta gtaagaaatg gggcgttact caaaatgtcc    420
aattcgactt tgtaaaagat aaaaaatata acaaagacgc tttaattgtt aaaatgcaag    480
gttttattaa ttccagaact tcattttcag atgtgaaggg tagtggatat gaattaacta    540
aacgaatgat ttggccattc caatataata taggactgac gactaaagat ccaaatgtta   600
gcttaatcaa ttaccttcct aaaaacaaaa tagaaactac tgatgttggt caaacattag    660
gatataacat tggaggtaat ttccagtcag caccatctat aggtggcaat ggctcattta    720
attattctaa aacaattagt tatacccaaa agagttatgt cagtgaagta gacaagcaaa    780
actcaaaatc tgttaaatgg ggtgttaaag caaacgaatt tgttacgcct gatggaaaaa    840
aatctgcgca tgatagatat ttattcgtac aaagtccaaa tggtccaaca ggttcagcaa    900
gagaatattt tgctcctgat aatcaattgc caccttagt tcaaagtggc tttaatccat     960
cgtttatcac tacactatca catgaaaaag gttcaagtga tacgagtgaa tttgaaattt   1020
catatggtag aaactagat attacatatg cgactttatt ccctagaact ggtatttacg    1080
cagaaagaaa gcataatgca tttgtaaata gaaactttgt agttagatat gaagttaatt   1140
ggaaaacaca cgaaattaaa gtgaaaggac ataattaa                            1178
```

<210> SEQ ID NO 23
<211> LENGTH: 283
<212> TYPE: PRT
<213> ORGANISM: Artificial Sequence
<220> FEATURE:
<223> OTHER INFORMATION: LukE

<400> SEQUENCE: 23

```
Asn Thr Asn Ile Glu Asn Ile Gly Asp Gly Ala Glu Val Ile Lys Arg
 1               5                  10                  15

Thr Glu Asp Val Ser Ser Lys Lys Trp Gly Val Thr Gln Asn Val Gln
             20                  25                  30

Phe Asp Phe Val Lys Asp Lys Lys Tyr Asn Lys Asp Ala Leu Ile Val
         35                  40                  45

Lys Met Gln Gly Phe Ile Asn Ser Arg Thr Ser Phe Ser Asp Val Lys
     50                  55                  60

Gly Ser Gly Tyr Glu Leu Thr Lys Arg Met Ile Trp Pro Phe Gln Tyr
 65                  70                  75                  80

Asn Ile Gly Leu Thr Thr Lys Asp Pro Asn Val Ser Leu Ile Asn Tyr
                 85                  90                  95

Leu Pro Lys Asn Lys Ile Glu Thr Thr Asp Val Gly Gln Thr Leu Gly
            100                 105                 110

Tyr Asn Ile Gly Gly Asn Phe Gln Ser Ala Pro Ser Ile Gly Gly Asn
        115                 120                 125

Gly Ser Phe Asn Tyr Ser Lys Thr Ile Ser Tyr Thr Gln Lys Ser Tyr
    130                 135                 140
```

```
Val Ser Glu Val Asp Lys Gln Asn Ser Lys Ser Val Lys Trp Gly Val
145                 150                 155                 160

Lys Ala Asn Glu Phe Val Thr Pro Asp Gly Lys Lys Ser Ala His Asp
                165                 170                 175

Arg Tyr Leu Phe Val Gln Ser Pro Asn Gly Pro Thr Gly Ser Ala Arg
            180                 185                 190

Glu Tyr Phe Ala Pro Asp Asn Gln Leu Pro Pro Leu Val Gln Ser Gly
        195                 200                 205

Phe Asn Pro Ser Phe Ile Thr Thr Leu Ser His Glu Lys Gly Ser Ser
    210                 215                 220

Asp Thr Ser Glu Phe Glu Ile Ser Tyr Gly Arg Asn Leu Asp Ile Thr
225                 230                 235                 240

Tyr Ala Thr Leu Phe Pro Arg Thr Gly Ile Tyr Ala Glu Arg Lys His
                245                 250                 255

Asn Ala Phe Val Asn Arg Asn Phe Val Val Arg Tyr Glu Val Asn Trp
            260                 265                 270

Lys Thr His Glu Ile Lys Val Lys Gly His Asn
        275                 280

<210> SEQ ID NO 24
<211> LENGTH: 114
<212> TYPE: DNA
<213> ORGANISM: Artificial Sequence
<220> FEATURE:
<223> OTHER INFORMATION: LukS signal peptide

<400> SEQUENCE: 24
atgaataata gtaaaattat ttctaaagtt ttattgtctt tatctctatt tactgtagga    60
gctagtgcat tgttattca agacgaactg atgcaaaaaa accatgcaaa agca          114

<210> SEQ ID NO 25
<211> LENGTH: 855
<212> TYPE: DNA
<213> ORGANISM: Artificial Sequence
<220> FEATURE:
<223> OTHER INFORMATION: LukS mature protein

<400> SEQUENCE: 25
gataacaata ttgagaatat tggtgatggc gctgaggtag tcaaaagaac agaagataca    60
agtagcgata agtgggggt cacacaaaat attcagtttg attttgttaa agataaaaag    120
tataacaaag acgctttgat tttaaaaatg caaggttta tcaattcaaa gactacttat    180
tacaattaca aaaacacaga tcatataaaa gcaatgaggt ggccttttca atacaatatt    240
ggtctcaaaa caaatgaccc caatgtagat ttaataaatt atctacctaa aaataaaata    300
gattcagtaa atgttagtca acattaggt tataacatag tggtaattt taatagtggt    360 ccatcaacag gaggtaatgg ttcatttaat tattcaaaaa caattagtta taatcaacaa    420
aactatatca gtgaagtaga acgtcaaaat tcaaaaagtg ttcaatgggg aataaaagct    480
aattcattta tcacatcatt aggtaaaatg tctggacatg atccaaattt atttgttgga    540
tataaaccat atagtcaaaa tccgagagac tattttgttc cagacaatga attaccccca    600
ttagtacaca gtggtttcaa tccttcattt attgcaactt tttctcatga aaaaggctca    660
ggagatacaa gtgaatttga ataacgtat ggcagaaata tggatgttac tcatgctact    720
agaagaacaa cacactatgg caatagttat ttagaaggat ctagaataca aacgcatttt    780
gtaaacagaa attacacagt taaatatgaa gtgaactgga aaactcatga aattaaagtg    840
```

-continued aaaggacata attga 855

<210> SEQ ID NO 26
<211> LENGTH: 1211
<212> TYPE: DNA
<213> ORGANISM: Artificial Sequence
<220> FEATURE:
<223> OTHER INFORMATION: ETA-LukS

<400> SEQUENCE: 26

```
aaatatcaac gtgagggctc tagtactaac gattttttt gtgcagtatg tagaatcact    60
gacaaggaac aaaagattaa aaatgaaaaa tattggggaa ctattgagtg gaattaacaa   120
acgtatttaa tgtttagtta attaaaagtt aataaaaaat aatttgtttt gaaatagaaa   180
cgttatataa tttttaatgt attcgaatac attaaaaaac gcaaatgtta ggatgattaa   240
taatgaataa tagtaaaatt atttctaaag ttttattgtc tttatctcta tttactgtag   300
gagctagtgc atttgttatt caagacgaac tgatgcaaaa aaaccatgca aaagcagata   360
acaatattga gaatattggt gatggcgctg aggtagtcaa agaacagaa gatacaagta    420
gcgataagtg gggggtcaca caaaatattc agtttgattt tgttaaagat aaaaagtata   480
acaaagacgc tttgatttta aaaatgcaag gttttatcaa ttcaaagact acttattaca   540
attacaaaaa cacagatcat ataaaagcaa tgaggtggcc tttccaatac aatattggtc   600
tcaaaacaaa tgaccccaat gtagatttaa taaattatct acctaaaaat aaaatagatt   660
cagtaaatgt tagtcaaaca ttaggttata acataggtgg taattttaat agtggtccat   720
caacaggagg taatggttca tttaattatt caaaaacaat tagttataat caacaaaact   780
atatcagtga agtagaacgt caaaattcaa aaagtgttca atggggaata aaagctaatt   840
catttatcac atcattaggt aaaatgtctg gacatgatcc aaatttattt gttggatata   900
aaccatatag tcaaaatccg agagactatt ttgttccaga caatgaatta ccccattag    960
tacacagtgg tttcaatcct tcatttattg caactgtttc tcatgaaaaa ggctcaggag  1020
atacaagtga atttgaaata acgtatggca gaaatatgga tgttactcat gctactagaa  1080
gaacaacaca ctatggcaat agttatttag aaggatctag aatacacaac gcatttgtaa  1140
acagaaatta cacagttaaa tatgaagtga actggaaaac tcatgaaatt aaagtgaaag  1200
gacataattg a                                                       1211
```

<210> SEQ ID NO 27
<211> LENGTH: 284
<212> TYPE: PRT
<213> ORGANISM: Artificial Sequence
<220> FEATURE:
<223> OTHER INFORMATION: LukS

<400> SEQUENCE: 27

Asp Asn Asn Ile Glu Asn Ile Gly Asp Gly Ala Glu Val Val Lys Arg
1               5                   10                  15

Thr Glu Asp Thr Ser Ser Asp Lys Trp Gly Val Thr Gln Asn Ile Gln
            20                  25                  30

Phe Asp Phe Val Lys Asp Lys Lys Tyr Asn Lys Asp Ala Leu Ile Leu
        35                  40                  45

Lys Met Gln Gly Phe Ile Asn Ser Lys Thr Thr Tyr Tyr Asn Tyr Lys
    50                  55                  60

Asn Thr Asp His Ile Lys Ala Met Arg Trp Pro Phe Gln Tyr Asn Ile
65                  70                  75                  80

-continued

```
Gly Leu Lys Thr Asn Asp Pro Asn Val Asp Leu Ile Asn Tyr Leu Pro
                 85              90                  95

Lys Asn Lys Ile Asp Ser Val Asn Val Ser Gln Thr Leu Gly Tyr Asn
            100             105                 110

Ile Gly Gly Asn Phe Asn Ser Gly Pro Ser Thr Gly Gly Asn Gly Ser
        115             120                 125

Phe Asn Tyr Ser Lys Thr Ile Ser Tyr Asn Gln Gln Asn Tyr Ile Ser
    130             135                 140

Glu Val Glu Arg Gln Asn Ser Lys Ser Val Gln Trp Gly Ile Lys Ala
145             150              155                 160

Asn Ser Phe Ile Thr Ser Leu Gly Lys Met Ser Gly His Asp Pro Asn
                165             170                 175

Leu Phe Val Gly Tyr Lys Pro Tyr Ser Gln Asn Pro Arg Asp Tyr Phe
            180             185                 190

Val Pro Asp Asn Glu Leu Pro Pro Leu Val His Ser Gly Phe Asn Pro
        195             200                 205

Ser Phe Ile Ala Thr Val Ser His Glu Lys Gly Ser Gly Asp Thr Ser
    210             215                 220

Glu Phe Glu Ile Thr Tyr Gly Arg Asn Met Asp Val Thr His Ala Thr
225             230             235                 240

Arg Arg Thr Thr His Tyr Gly Asn Ser Tyr Leu Glu Gly Ser Arg Ile
                245             250                 255

His Asn Ala Phe Val Asn Arg Asn Tyr Thr Val Lys Tyr Glu Val Asn
            260             265                 270

Trp Lys Thr His Glu Ile Lys Val Lys Gly His Asn
        275             280
```